US011236365B2

(12) United States Patent
Inoue et al.

(10) Patent No.: US 11,236,365 B2
(45) Date of Patent: Feb. 1, 2022

(54) METHOD FOR PRODUCING POLYISOPRENOID, TRANSFORMED PLANT, METHOD FOR PRODUCING PNEUMATIC TIRE AND METHOD FOR PRODUCING RUBBER PRODUCT

(71) Applicants: SUMITOMO RUBBER INDUSTRIES, LTD., Kobe (JP); TOHOKU University, Sendai (JP)

(72) Inventors: Yukino Inoue, Kobe (JP); Haruhiko Yamaguchi, Kobe (JP); Kazuhisa Fushihara, Kobe (JP); Seiji Takahashi, Sendai (JP); Satoshi Yamashita, Sendai (JP); Toru Nakayama, Sendai (JP)

(73) Assignees: SUMITOMO RUBBER INDUSTRIES, LTD., Kobe (JP); TOHOKU UNIVERSITY, Sendai (JP)

( * ) Notice: Subject to any disclaimer, the term of this patent is extended or adjusted under 35 U.S.C. 154(b) by 193 days.

(21) Appl. No.: 16/502,750

(22) Filed: Jul. 3, 2019

(65) Prior Publication Data
US 2019/0323039 A1 Oct. 24, 2019

Related U.S. Application Data

(62) Division of application No. 15/170,584, filed on Jun. 1, 2016, now Pat. No. 10,385,362.

(30) Foreign Application Priority Data

Jun. 30, 2015 (JP) ................................. 2015-131022

(51) Int. Cl.
| | | |
|---|---|---|
| *C12N 15/82* | (2006.01) | |
| *C12P 5/00* | (2006.01) | |
| *C12N 9/10* | (2006.01) | |
| *B29D 30/08* | (2006.01) | |
| *B29D 30/06* | (2006.01) | |
| *C07K 14/415* | (2006.01) | |
| *B29K 607/00* | (2006.01) | |

(52) U.S. Cl.
CPC .......... *C12P 5/007* (2013.01); *B29D 30/0601* (2013.01); *B29D 30/08* (2013.01); *C07K 14/415* (2013.01); *C12N 9/1085* (2013.01); *C12N 15/8243* (2013.01); *B29K 2607/00* (2013.01); *C12Y 205/0102* (2013.01)

(58) Field of Classification Search
None
See application file for complete search history.

(56) References Cited

U.S. PATENT DOCUMENTS

| | | | |
|---|---|---|---|
| 9,127,286 | B2 | 9/2015 | Nakazawa et al. |
| 10,000,774 | B2 | 6/2018 | Yamaguchi |
| 10,385,362 | B2 | 8/2019 | Inoue et al. |
| 2003/0236208 | A1* | 12/2003 | Kmiec ................. C12N 15/102 514/44 R |
| 2010/0218272 | A1 | 8/2010 | Nakazawa et al. |
| 2011/0201771 | A1 | 8/2011 | Puskas et al. |
| 2015/0266988 | A1 | 9/2015 | Kojima et al. |
| 2017/0051313 | A1 | 2/2017 | Inoue et al. |
| 2018/0171364 | A1 | 6/2018 | Yamaguchi et al. |

FOREIGN PATENT DOCUMENTS

| | | |
|---|---|---|
| CN | 104684987 A | 6/2015 |
| EP | 3097775 A1 | 11/2016 |
| JP | 2003-18999 A | 1/2003 |
| JP | 2003-310295 A | 11/2003 |
| JP | 2005-500840 A | 1/2005 |
| JP | 2005-225796 A | 8/2005 |
| JP | 2005-308412 A | 11/2005 |
| JP | 2005-312436 A | 11/2005 |
| JP | 2009-221306 A | 10/2009 |
| JP | 2010-119373 A | 6/2010 |
| JP | 2010-132594 A | 6/2010 |
| JP | 2011-52146 A | 3/2011 |
| JP | 2011-188776 A | 9/2011 |
| JP | 5035871 B2 | 9/2012 |
| JP | 2014-11972 A | 1/2014 |
| JP | 5383197 B2 | 1/2014 |
| JP | 2014-227487 A | 12/2014 |

(Continued)

OTHER PUBLICATIONS

Sunderasan et al., 1994, Incidence of Self- and Cross-pollination in Two Hevea brasiliensis clones, J. Nat. Rubb. Res. 9(4): 253-257.*
Results from BLAST® search for sequences producing significant alignments relative to SEQ ID No. 1 in the GenBank, obtained on Jun. 28, 2021.*
Results from BLAST® search for sequences producing significant alignments relative to SEQ ID No. 3 in the GenBank, obtained on Jun. 28, 2021.*
Results from BLAST® search for sequences producing significant alignments relative to SEQ ID No. 5 in the GenBank, obtained on Jun. 28, 2021.*
Aoki et al., "Identification of Laticifer-specific Genes and their Promoter Regions from a Natural Rubber Producing Plant *Hevea brasiliensis*," Plant Science, vol. 225, 2014 (Available online May 12, 2014), pp. 1-8.

(Continued)

*Primary Examiner* — Bratislav Stankovic
(74) *Attorney, Agent, or Firm* — Birch, Stewart, Kolasch & Birch, LLP

(57) ABSTRACT

Provided is a method for producing a polyisoprenoid, which can increase natural rubber production by enhancing the rubber synthesis activity of rubber particles. The present invention provides methods for producing a polyisoprenoid using a gene coding for a cis-prenyltransferase (CPT) family protein, a gene coding for a Nogo-B receptor (NgBR) family protein and a gene coding for a rubber elongation factor (REF) family protein, specifically a method for producing a polyisoprenoid in vitro using rubber particles bound to proteins coded for by these genes, and a method for producing a polyisoprenoid in vivo using a recombinant organism (plant) having these genes introduced therein.

6 Claims, 2 Drawing Sheets

Specification includes a Sequence Listing.

(56) References Cited

FOREIGN PATENT DOCUMENTS

| JP | 2015-136296 A | 7/2015 |
|---|---|---|
| JP | 2016-93186 A | 5/2016 |
| JP | 2016-149973 A | 8/2016 |
| JP | 2016-154458 A | 9/2016 |
| WO | WO 03/010294 A2 | 2/2003 |

OTHER PUBLICATIONS

Asawatreratanakul et al., "Molecular cloning, expression and characterization of cDNA encoding cis-prenyltransferases from Hevea brasiliensis A key factor participating in natural rubber biosynthesis," European Journal of Biochemistry, vol. 270, 2003, pp. 4671-4680.
Berthelot et al., "Hevea brasiliensis REF (Hev b 1) and SRPP (Hev b 3): An Overview on Rubber Particle Proteins," Biochimie, vol. 106, 2014 (Available online Jul. 11, 2014), pp. 1-9.
Branden et al., "Introduction to Protein Structure," Garland Publishing Inc., New York, 1991, p. 247 (3 pages total).
Brasher et al., "A Two-component Enzyme Complex is Required for Dolichol Biosynthesis in Tomato," The Plant Journal, vol. 82, 2015 (published online Apr. 21, 2015), pp. 903-914.
Dai et al., "In-depth proteome analysis of the rubber particle of Hevea brasiliensis (para rubber tree)," Plant Molecular Biology, vol. 82, 2013 (published online Apr. 4, 2013), pp. 155-168.
Epping et al., "A rubber transferase activator is necessary for natural rubber biosynthesis in dandelion," Nature Plants, vol. 1, Article No. 15048, May 2015 (published Apr. 27, 2015), XP055372960, pp. 1-9.
Goodman, "Polymer biosynthesis: Rubber ramps up," Nature Chemical Biology, vol. 11, No. 7, Jul. 2015, p. 448, XP055373184.
Harrison et al., "Nogo-B receptor is necessary for cellular dolichol biosynthesis and protein N-glycosylation," The EMBO Journal, vol. 30, No. 12, 2011 (published online May 13, 2011), pp. 2490-2500.
Hillebrand et al., "Down-Regulation of Small Rubber Particle Protein Expression Affects Integrity of Rubber Particles and Rubber Content in Taraxacum brevicorniculatum," PLoS ONE, vol. 7, Issue 7, e41874, Jul. 23, 2012, pp. 1-9.
Hoffman et al., "The Who, What, and Where of Plant Polyprenol Biosynthesis Point to Thylakoid Membranes and Photosynthetic Performance," The Plant Cell, vol. 29, Jul. 2017, pp. 1552-1553.
Laibach et al., "Identification of a Taraxacum Brevicorniculatum Rubber Elongation Factor Protein that is Localized on Rubber Particles and Promotes Rubber Biosynthesis," The Plant Journal, vol. 82, 2015 (published online Mar. 24, 2015), pp. 609-620.
Madin et al., "A Highly Efficient and Robust Cell-free Protein Synthesis System Prepared from Wheat Embryos: Plants Apparently Contain a Suicide System Directed at Ribosomes," Proceedings of] the National Academy of Sciences USA, vol. 97, No. 2, Jan. 18, 2000, pp. 559-564 (7 pages total).
Nguyen et al., "cis-Prenyltransferase Interacts with a Nogo-B Receptor Homolog for Dolichol Biosynthesis in Panax ginseng Meyer," Journal of Ginseng Research, vol. 41, 2017 (Available online Jan. 27, 2017), pp. 403-410.
Ohya et al., "Biosynthesis of Natural Rubber and Other Natural Polyisoprenoids," Biopolymers Online, Published online Jan. 15, 2005, 43 pages.
Park et al., "Mutation of Nogo-B receptor, a subunit of cis-prenyltransferase, causes a congenital disorder of glycosylation," Cell Metabolism, vol. 20, Sep. 2, 2014 (published Jul. 24, 2014), pp. 448-457.
Post et al., "Laticifer-Specific cis-Prenyltransferase Silencing Affects the Rubber, Triterpene, and Inulin Content of Taraxacum brevicorniculatum," Plant Physiology, Mar. 2012, vol. 158, pp. 1406-1417.
Priya et al., "Differential expression pattern of rubber elongation factor (REF) mRNA transcripts from high and low yielding clones of rubber tree (Hevea brasiliensis Muell. Arg.)," Plant Cell Reports, vol. 26, 2007 (Published online Jul. 14, 2007), pp. 1833-1838.
Priya et al., "Molecular Cloning and Characterization of the Rubber Elongation Factor Gene and its Promoter Sequence from Rubber Tree (Hevea brasiliensis): A Gene Involved in Rubber Biosynthesis," Plant Science, vol. 171, 2006 (published online Jun. 13, 2006), pp. 470-480.
Qu et al., "A lettuce (Lactuca sativa) homolog of human Nogo-B receptor interacts with cis-prenyltransferase and is necessary for natural rubber biosynthesis," J. Biol. Chem., vol. 290, No. 4, Jan. 23, 2015, 2 pages, abstract provided only.
Qu et al., 2013, The Journal of Biological Chemistry, vol. 290, pp. 1898-1914.
Rahman et al., "Draft genome sequence of the rubber tree Hevea brasiliensis," BMC Genomics, vol. 14, No. 75, 2013, pp. 1-15.
Rahman et al., "TSA: Hevea brasiliensis contig33814, mRNA sequence," Database GenBank [online], Accession No. JT945746, Feb. 5, 2013, pp. 1-2.
Rojruthai et al., "In Vitro Synthesis of High Molecular Weight Rubber by Hevea Small Rubber Particles," Journal of Bioscience and Bioengineering, vol. 109, No. 2, 2010 (Available online Sep. 18, 2009), pp. 107-114.
Surmacz et al., "cis-Prenyltransferase AtCPT6 produces a family of very short-chain polyisoprenoids in planta," Biochimica et Biophysica Acta, vol. 1841, 2014 (available online Dec. 1, 2013), pp. 240-250.
Takahashi et al., "Characterization of cis-prenyltransferases from the rubber producing plant Hevea brasiliensis heterologously expressed in yeast and plant cells," Plant Biotechnology, vol. 29, Oct. 20, 2012 (published online Aug. 30, 2012), pp. 411-417 (8 pages total).
Tata et al., "Lacticifer Tissue-Specific Activation of the Hevea SRPP Promoter in Taraxacum brevicorniculatum and its Regulation by Light, Tapping and Cold Stress," Industrial Crops and Products, vol. 40, 2012, pp. 219-224.
Xiang et al., "Proteome Analysis of the Large and the Small Rubber Particles of Hevea brasiliensis Using 2D-DIGE," Plant Physiology and Biochemistry, vol. 60, 2012 (Available online Sep. 5, 2012), pp. 207-213.
International Preliminary Report on Patentability and Written Opinion of the International Searching Authority for International Application No. PCT/JP2017/041732, dated Jun. 25, 2019.
International Search Report for International Application No. PCT/JP2016/069172, dated Sep. 6, 2016, with English translation.
International Search Report for International Application No. PCT/JP2016/065942, dated Jun. 28, 2016.
International Search Report for International Application No. PCT/JP2017/041732, dated Feb. 20, 2018.
Phatthiya et al., "Cloning and Expression of the Gene Encoding Solanesyl Diphosphate Synthase from Hevea Brasiliensis", Plant Science, vol. 172, 2007, pp. 824-831.
Takahashi et al., "Molecular Insights of Natural Rubber Biosynthesis—An Approach from Prenyltransferase Gene Analysis", The Society of Rubber Science and Technology, vol. 76, No. 12, 2003, pp. 446-452, with 1 page abstract.
Unknown, "Successful in Vitro Synthesis of Natural Rubber by Bioengineering—Contributing to the Stable Supply of Natural Rubber with New Molecular Structure", Tohoku University, Nov. 16, 2016, 4 pages total.
Yamashita et al., "Identification and Reconstitution of the Rubber Biosynthetic Machinery on Rubber Particles from Hevea Brasiliensis", eLife, vol. 5, No. 19022, Oct. 28, 2016, pp. 1-28.
Yokoyama, "Development of Membrane Protein-synthesizing System Without Using Cells", NPG Nature Asia-Pacific, vol. 7, No. 4-5, 2010, pp. 28-29, with English translation.
Montoro, Pascal et al., "Biotechnologies in rubber tree (Hevea brasiliensis)", Asian Pacific Conference on Tissue Culture and Agribiotechnology, Malaysia, Jun. 17-21, 2007, pp. 1-3.

\* cited by examiner

Natural rubber

METHOD FOR PRODUCING POLYISOPRENOID, TRANSFORMED PLANT, METHOD FOR PRODUCING PNEUMATIC TIRE AND METHOD FOR PRODUCING RUBBER PRODUCT

CROSS REFERENCE TO RELATED APPLICATIONS

This application is a Divisional of copending application Ser. No. 15/170,584, filed on Jun. 1, 2016, which claims priority under 35 U.S.C. § 119(a) to Application No. 2015-131022, filed in Japan on Jun. 30, 2015, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "2019-06-13_Sequence_Listing_5051-0413PUS2.txt" created on Nov. 1, 2016 and is 10,519 bytes in size. The sequence listing contained in this .txt file is part of the specification and is hereby incorporated by reference herein in its entirety.

TECHNICAL FIELD

The present invention relates to a method for producing a polyisoprenoid, a transformed plant, a method for producing a pneumatic tire, and a method for producing a rubber product.

BACKGROUND ART

Nowadays natural rubber (one example of polyisoprenoids) for use in industrial rubber products are obtained by cultivating rubber-producing plants, such as para rubber tree (*Hevea brasiliensis*) belonging to the family Euphorbiaceae, or Indian rubber tree (*Ficus elastica*) belonging to the family Moraceae, to biosynthesize natural rubber by the lactiferous cells of the plants, and harvesting the natural rubber by hand from the plants.

At present, *Hevea brasiliensis* is practically the only one source of natural rubber for industrial rubber products. *Hevea brasiliensis* is a plant that can grow only in limited areas such as in Southeast Asia and South America. Conventionally, natural rubber production has been increased by applying ethephon or methyl jasmonate to *Hevea brasiliensis* trees to induce lactiferous duct formation. Moreover, *Hevea brasiliensis* requires about seven years from planting to mature enough for rubber extraction, and the period during which natural rubber can be extracted is limited to 20 to 30 years. Although more natural rubber is expected to be demanded mainly by developing countries in years to come, for the reason mentioned above it is difficult to greatly increase the production of natural rubber using *Hevea brasiliensis*. Depletion of natural rubber sources is therefore of concern, and there are needs for stable natural rubber sources other than mature *Hevea brasiliensis* and for improvement in productivity of natural rubber from *Hevea brasiliensis*.

Natural rubber has a cis-1,4-polyisoprene structure formed mainly of isopentenyl diphosphate (IPP) units, and the nature of this structure suggests that cis-prenyltransferase (CPT) is involved in natural rubber biosynthesis. For example, several CPTs are found in *Hevea brasiliensis*, including *Hevea* rubber transferase 1 (HRT1) and *Hevea* rubber transferase 2 (HRT2) (see for example Non Patent Literatures 1 and 2). It is also known that rubber synthesis can be reduced in the dandelion species *Taraxacum brevicorniculatum* by suppressing CPT expression (see for example Non Patent Literature 3).

Previous studies of proteins associated with natural rubber biosynthesis have focused on rubber elongation factor (REF) and small rubber particle protein (SRPP) (see for example Non Patent Literatures 4 and 5). However, the associations between these proteins and CPT are not completely understood.

It has also been suggested that Nogo-B receptor (NgBR) is involved in dolichol biosynthesis by a human CPT (see for example Non Patent Literature 6).

Methods have been studied for increasing the production of natural rubber in *Hevea brasiliensis*, but since the rubber synthesis mechanism of *Hevea brasiliensis* is not completely understood, *Hevea brasiliensis* variants have been proposed which have been genetically modified to express and enhance genes of the known monomer (isopentenyl diphosphate) synthesis pathways (mevalonate (MVA) pathway and non-mevalonate (MEP) pathway) (see for example Patent Literature 1).

CITATION LIST

Patent Literature

Patent Literature 1: JP 2005-500840 T

Non Patent Literature

Non Patent Literature 1: Rahaman et al., BMC Genomics, 2013, vol. 14
Non Patent Literature 2: Asawatreratanakul et al., European Journal of Biochemistry, 2003, vol. 270, pp. 4671-4680
Non Patent Literature 3: Post et al., Plant Physiology, 2012, vol. 158, pp. 1406-1417
Non Patent Literature 4: Hillebrand et al., PLoS ONE, 2012, vol. 7
Non Patent Literature 5: Priya et al., Plant Cell Reports, 2007, vol. 26, pp. 1833-1838
Non Patent Literature 6: K. D. Harrison et al., The EMBO Journal, 2011, vol. 30, pp. 2490-2500

SUMMARY OF INVENTION

Technical Problem

As described above, there are needs for development of stable natural rubber sources other than mature *Hevea brasiliensis* and for improvement in productivity of natural rubber from *Hevea brasiliensis*, but at present, the biosynthesis mechanism of natural rubber, and particularly the regulatory mechanism remains largely unclear, and there is still much room for improvement to greatly increase natural rubber production.

Although methods have been studied for increasing the production of natural rubber in *Hevea brasiliensis* as described above, it is known that ethephon, methyl jasmonate and other chemicals need to be applied to *Hevea brasiliensis* trees continuously, but long-term application of such chemicals may damage the trees. For example, it is known that bark splitting is more likely to occur when ethephon is applied to the trunk of *Hevea brasiliensis* trees for a long period of time.

Moreover, even when the genes of the monomer (isopentenyl diphosphate) synthesis pathways (mevalonate (MVA) pathway and non-mevalonate (MEP) pathway) are expressed and enhanced, since the monomer material isopentenyl diphosphate (IPP) has uses apart from a raw material of natural rubber, the increase in IPP production may not lead to increased natural rubber production.

Thus, at present the biosynthesis mechanism of natural rubber, and particularly the regulatory mechanism remains largely unclear, and there is still much room for improvement to greatly increase natural rubber production.

In this context, one possible approach to solving these problems is to stabilize and enhance the activity of CPT in natural rubber biosynthesis in order to increase natural rubber production.

It is an object of the present invention to resolve these problems and provide a method for producing a polyisoprenoid, which can increase natural rubber production by enhancing the rubber synthesis activity of rubber particles in vitro.

It is another object of the present invention to resolve these problems and provide a method for producing a polyisoprenoid, which can increase natural rubber production by producing a transformed plant with enhanced rubber synthesis activity.

Solution to Problem

The present invention relates to a method for producing a polyisoprenoid, the method including a step of binding a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein to rubber particles in vitro. This invention is hereinafter called the first aspect of the present invention, and is also referred to simply as the first invention.

At least one selected from the group consisting of the gene coding for a cis-prenyltransferase (CPT) family protein, the gene coding for a Nogo-B receptor (NgBR) family protein, and the gene coding for a rubber elongation factor (REF) family protein is preferably derived from a plant.

At least one selected from the group consisting of the gene coding for a cis-prenyltransferase (CPT) family protein, the gene coding for a Nogo-B receptor (NgBR) family protein, and the gene coding for a rubber elongation factor (REF) family protein is preferably derived from *Hevea brasiliensis*.

The binding step preferably includes performing protein synthesis in the presence of both rubber particles and a cell-free protein synthesis solution containing an mRNA coding for a cis-prenyltransferase (CPT) family protein, an mRNA coding for a Nogo-B receptor (NgBR) family protein, and an mRNA coding for a rubber elongation factor (REF) family protein, to bind the CPT family protein, the NgBR family protein, and the REF family protein to the rubber particles.

The cell-free protein synthesis solution preferably contains a germ extract.

The germ extract is preferably derived from wheat.

The rubber particles are preferably present in the cell-free protein synthesis solution at a concentration of 5 to 50 g/L.

The first invention also relates to a method for producing a pneumatic tire, the method including the steps of: kneading a polyisoprenoid produced by the method for producing a polyisoprenoid of the first invention with an additive to obtain a kneaded mixture; building a green (or raw) tire from the kneaded mixture; and vulcanizing the green tire.

The first invention also relates to a method for producing a rubber product, the method including the steps of: kneading a polyisoprenoid produced by the method for producing a polyisoprenoid of the first invention with an additive to obtain a kneaded mixture; forming a raw rubber product from the kneaded mixture; and vulcanizing the raw rubber product.

The present invention also relates to a method for producing a polyisoprenoid, the method including producing a polyisoprenoid in a transformed plant produced by introducing a gene coding for a cis-prenyltransferase (CPT) family protein, a gene coding for a Nogo-B receptor (NgBR) family protein, and a gene coding for a rubber elongation factor (REF) family protein into a plant to allow the plant to express the CPT family protein, the NgBR family protein, and the REF family protein. This invention is hereinafter called the second aspect of the present invention, and is also referred to simply as the second invention.

At least one selected from the group consisting of the gene coding for a cis-prenyltransferase (CPT) family protein, the gene coding for a Nogo-B receptor (NgBR) family protein, and the gene coding for a rubber elongation factor (REF) family protein is preferably derived from a plant.

At least one selected from the group consisting of the gene coding for a cis-prenyltransferase (CPT) family protein, the gene coding for a Nogo-B receptor (NgBR) family protein, and the gene coding for a rubber elongation factor (REF) family protein is preferably derived from *Hevea brasiliensis*.

The gene coding for a cis-prenyltransferase (CPT) family protein is preferably the following DNA [1] or [2]:

[1] a DNA having the nucleotide sequence of SEQ ID NO:1; or

[2] a DNA that hybridizes under stringent conditions with a DNA having a nucleotide sequence complementary to the nucleotide sequence of SEQ ID NO:1, and codes for a protein having an enzyme activity that catalyzes a reaction of cis-chain elongation of an isoprenoid compound.

The gene coding for a Nogo-B receptor (NgBR) family protein is preferably the following DNA [3] or [4]:

[3] a DNA having the nucleotide sequence of SEQ ID NO:3; or

[4] a DNA that hybridizes under stringent conditions with a DNA having a nucleotide sequence complementary to the nucleotide sequence of SEQ ID NO:3, and codes for a protein having the functions of binding to a membrane via one or more transmembrane domains on the N-terminal side of the protein, and interacting with another protein on the C-terminal side thereof.

The gene coding for a rubber elongation factor (REF) family protein is preferably the following DNA [5] or [6]:

[5] a DNA having the nucleotide sequence of SEQ ID NO:5; or

[6] a DNA that hybridizes under stringent conditions with a DNA having a nucleotide sequence complementary to the nucleotide sequence of SEQ ID NO:5, and codes for a rubber particle-associated protein that is bound to rubber particles in latex.

The second invention also relates to a transformed plant, produced by introducing a gene coding for a cis-prenyltransferase (CPT) family protein, a gene coding for a Nogo-B receptor (NgBR) family protein, and a gene coding for a rubber elongation factor (REF) family protein into a plant to allow the plant to express the CPT family protein, the NgBR family protein, and the REF family protein.

At least one selected from the group consisting of the gene coding for a cis-prenyltransferase (CPT) family protein, the gene coding for a Nogo-B receptor (NgBR) family protein, and the gene coding for a rubber elongation factor (REF) family protein is preferably derived from a plant.

At least one selected from the group consisting of the gene coding for a cis-prenyltransferase (CPT) family protein, the gene coding for a Nogo-B receptor (NgBR) family protein, and the gene coding for a rubber elongation factor (REF) family protein is preferably derived from *Hevea brasiliensis*.

The gene coding for a cis-prenyltransferase (CPT) family protein is preferably the following DNA [1] or [2]:

[1] a DNA having the nucleotide sequence of SEQ ID NO:1; or

[2] a DNA that hybridizes under stringent conditions with a DNA having a nucleotide sequence complementary to the nucleotide sequence of SEQ ID NO:1, and codes for a protein having an enzyme activity that catalyzes a reaction of cis-chain elongation of an isoprenoid compound.

The gene coding for a Nogo-B receptor (NgBR) family protein is preferably the following DNA [3] or [4]:

[3] a DNA having the nucleotide sequence of SEQ ID NO:3; or

[4] a DNA that hybridizes under stringent conditions with a DNA having a nucleotide sequence complementary to the nucleotide sequence of SEQ ID NO:3, and codes for a protein having the functions of binding to a membrane via one or more transmembrane domains on the N-terminal side of the protein, and interacting with another protein on the C-terminal side thereof.

The gene coding for a rubber elongation factor (REF) family protein is preferably the following DNA [5] or [6]:

[5] a DNA having the nucleotide sequence of SEQ ID NO:5; or

[6] a DNA that hybridizes under stringent conditions with a DNA having a nucleotide sequence complementary to the nucleotide sequence of SEQ ID NO:5, and codes for a rubber particle-associated protein that is bound to rubber particles in latex.

The second invention also relates to a method for producing a pneumatic tire, the method including the steps of: kneading a polyisoprenoid produced by the method for producing a polyisoprenoid of the second invention with an additive to obtain a kneaded mixture; building a green tire from the kneaded mixture; and vulcanizing the green tire.

The second invention also relates to a method for producing a rubber product, the method including the steps of: kneading a polyisoprenoid produced by the method for producing a polyisoprenoid of the second invention with an additive to obtain a kneaded mixture; forming a raw rubber product from the kneaded mixture; and vulcanizing the raw rubber product.

Advantageous Effects of Invention

The method for producing a polyisoprenoid of the first invention includes a step of binding a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein to rubber particles in vitro. Binding the CPT family protein, NgBR family protein, and REF family protein to rubber particles is expected to stabilize and enhance the activity of the CPT family protein, thereby enhancing the rubber synthesis activity of rubber particles. Thus, it is possible to produce rubber more efficiently in reaction vessels (e.g. test tubes, industrial plants).

The method for producing a pneumatic tire of the first invention includes the steps of: kneading a polyisoprenoid produced by the method for producing a polyisoprenoid of the first invention with an additive to obtain a kneaded mixture; building a green tire from the kneaded mixture; and vulcanizing the green tire. With this method, a pneumatic tire is produced from a polyisoprenoid produced by a method that produces a polyisoprenoid with high productivity. Thus, it is possible to use plant resources effectively to produce an environmentally friendly pneumatic tire.

The method for producing a rubber product of the first invention includes the steps of: kneading a polyisoprenoid produced by the method for producing a polyisoprenoid of the first invention with an additive to obtain a kneaded mixture; forming a raw rubber product from the kneaded mixture; and vulcanizing the raw rubber product. With this method, a rubber product is produced from a polyisoprenoid produced by a method that produces a polyisoprenoid with high productivity. Thus, it is possible to use plant resources effectively to produce an environmentally friendly rubber product.

The method for producing a polyisoprenoid of the second invention includes producing a polyisoprenoid in a transformed plant produced by introducing a gene coding for a cis-prenyltransferase (CPT) family protein, a gene coding for a Nogo-B receptor (NgBR) family protein, and a gene coding for a rubber elongation factor (REF) family protein into a plant to allow the plant to express the CPT family protein, the NgBR family protein, and the REF family protein. According to this method, since the CPT family protein, NgBR family protein, and REF family protein are co-expressed, the activity of the CPT family protein is expected to be stabilized and enhanced. Therefore, it is expected that the transformed plant engineered to co-express the CPT family protein, NgBR family protein, and REF family protein exhibits continuously enhanced rubber synthesis activity, and the use of such a transformed plant in polyisoprenoid production can result in an increase in polyisoprenoid production.

The method for producing a pneumatic tire of the second invention includes the steps of: kneading a polyisoprenoid produced by the method for producing a polyisoprenoid of the second invention with an additive to obtain a kneaded mixture; building a green tire from the kneaded mixture; and vulcanizing the green tire. With this method, a pneumatic tire is produced from a polyisoprenoid produced by a method that produces a polyisoprenoid with high productivity. Thus, it is possible to use plant resources effectively to produce an environmentally friendly pneumatic tire.

The method for producing a rubber product of the second invention includes the steps of: kneading a polyisoprenoid produced by the method for producing a polyisoprenoid of the second invention with an additive to obtain a kneaded mixture; forming a raw rubber product from the kneaded mixture; and vulcanizing the raw rubber product. With this method, a rubber product is produced from a polyisoprenoid produced by a method that produces a polyisoprenoid with high productivity. Thus, it is possible to use plant resources effectively to produce an environmentally friendly rubber product.

DESCRIPTION OF EMBODIMENTS

Herein, the first invention and the second invention are also referred to collectively as the present invention. The first invention will be explained first, and then the second invention will be explained.

First Invention

The method for producing a polyisoprenoid of the first invention includes a step of binding a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein to rubber particles in vitro.

Figure 1:
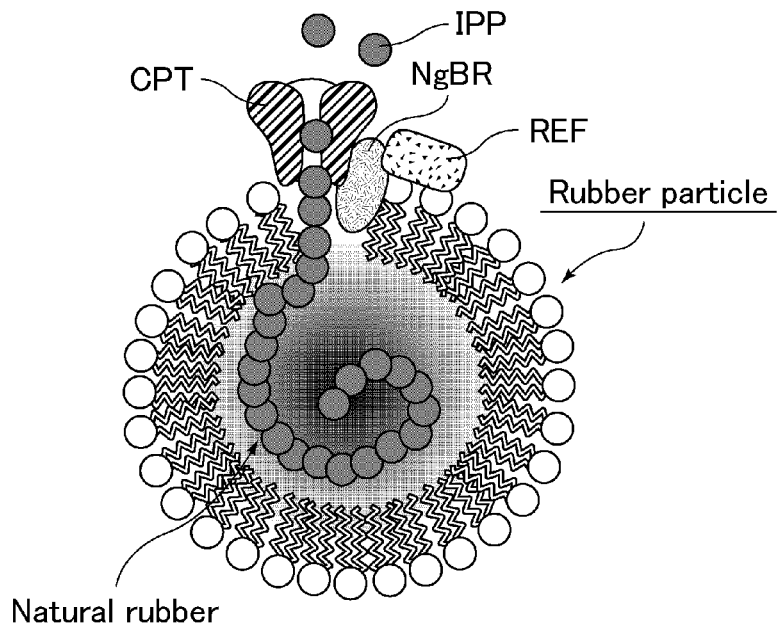
FIG. 1 is a presumptive diagram of rubber synthesis by CPT, NgBR, and REF on a rubber particle.

The inventors were the first to discover that the rubber synthesis of rubber particles is activated by binding a CPT family protein, a NgBR family protein, and a REF family protein to rubber particles in vitro. The inventors have also discovered here for the first time that the combination of the CPT family protein, NgBR family protein, and REF family protein is directly involved in rubber synthesis. It is presumed that the CPT family protein, NgBR family protein, and REF family protein are disposed on rubber particle for rubber synthesis as shown in FIG. 1. FIG. 1 illustrates an example of rubber synthesis in which CPT, NgBR, and REF are shown as the CPT family protein, NgBR family protein, and REF family protein, respectively, and the isopentenyl diphosphate (IPP) substrate is polymerized by CPT to synthesize natural rubber within a rubber particle.

Hence, the rubber synthesis activity of rubber particles can be enhanced by binding a CPT family protein, a NgBR family protein, and a REF family protein to rubber particle in vitro, for example in reaction vessels (e.g. test tubes, industrial plants) as in the production method of the first invention. Thus, it is possible to produce rubber more efficiently in reaction vessels (e.g. test tubes, industrial plants).

The production method of the first invention may include any other step as long as it involves the above binding step, and each step may be performed once or repeated multiple times.

The amounts of the CPT family protein, NgBR family protein, and REF family protein to be bound to the rubber particles are not particularly limited in the first invention.

Herein, binding of a CPT family protein, a NgBR family protein, and a REF family protein to rubber particles means that, for example, all or part of the CPT family protein, NgBR family protein, and REF family protein is incorporated into the rubber particles, or inserted into the membrane structure of the rubber particles. It is not limited to these embodiments and also includes embodiments in which, for example, the proteins are localized on the surface or inside of the rubber particles. Moreover, the concept of binding to rubber particle also includes embodiments in which the CPT family protein, NgBR family protein, and REF family protein form a complex with another protein bound to the rubber particles as described above, so as to be present in the form of the complex on the rubber particles.

The origin of the rubber particles is not particularly limited. For example, the rubber particles may be derived from the latex of a rubber-producing plant such as *Hevea brasiliensis, Taraxacum kok-saghyz, Parthenium argentatum, Sonchus oleraceus,* or *Ficus elastica.*

The particle size of the rubber particles is also not particularly limited. Rubber particles of a specific particle size may be sorted out and used, or a mixture of rubber particles of different particle sizes may be used. When rubber particles of a specific particle size are sorted out and used, the rubber particles may be either small rubber particles (SRP) with a small particle size or large rubber particles (LRP) with a large particle size.

Commonly used methods may be employed for sorting out the rubber particles of a specific particle size, including, for example, a method involving centrifugation, preferably multistage centrifugation. A specific method includes centrifugation at 500-1500×g, centrifugation at 1700-2500×g, centrifugation at 7000-9000×g, centrifugation at 15000-25000×g, and centrifugation at 40000-60000×g, carried out in that order. The treatment time for each centrifugation treatment is preferably at least 20 minutes, more preferably at least 30 minutes, still more preferably at least 40 minutes, but preferably 120 minutes or less, more preferably 90 minutes or less. The treatment temperature for each centrifugation treatment is preferably 0° C. to 10° C., more preferably 2° C. to 8° C., particularly preferably 4° C.

In the binding step, a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein are bound to rubber particles in vitro.

The origins of the gene coding for a cis-prenyltransferase (CPT) family protein, the gene coding for a Nogo-B receptor (NgBR) family protein, and the gene coding for a rubber elongation factor (REF) family protein are not particularly limited, but they are each preferably derived from plants, more preferably at least one selected from the group consisting of plants of the genera *Hevea, Sonchus, Taraxacum,* and *Parthenium.* Among these, they are each still more preferably derived from at least one species of plant selected from the group consisting of *Hevea brasiliensis, Sonchus oleraceus, Parthenium argentatum,* and *Taraxacum kok-saghyz,* particularly preferably *Hevea brasiliensis.* Most preferably, they are all derived from *Hevea brasiliensis.*

The plant is not particularly limited, and examples include *Hevea* species such as *Hevea brasiliensis; Sonchus* species such as *Sonchus oleraceus, Sonchus asper,* and *Sonchus brachyotus; Solidago* species such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea,* and *Solidago gigantea* Ait. var. *leiophylla* Fernald; *Helianthus* species such as *Helianthus annus, Helianthus argophyllus, Helianthus atrorubens, Helianthus debilis, Helianthus decapetalus,* and *Helianthus giganteus; Taraxacum* species such as dandelion *(Taraxacum), Taraxacum venustum* H. Koidz, *Taraxacum hondoense* Nakai, *Taraxacum platycarpum* Dahlst, *Taraxacum japonicum, Taraxacum officinale* Weber, and *Taraxacum kok-saghyz; Ficus* species such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis; Parthenium* species such as *Parthenium argentatum,* and *Parthenium hysterophorus, Ambrosia artemisiifolia;* and lettuce *(Lactuca sativa).*

Figure 2:
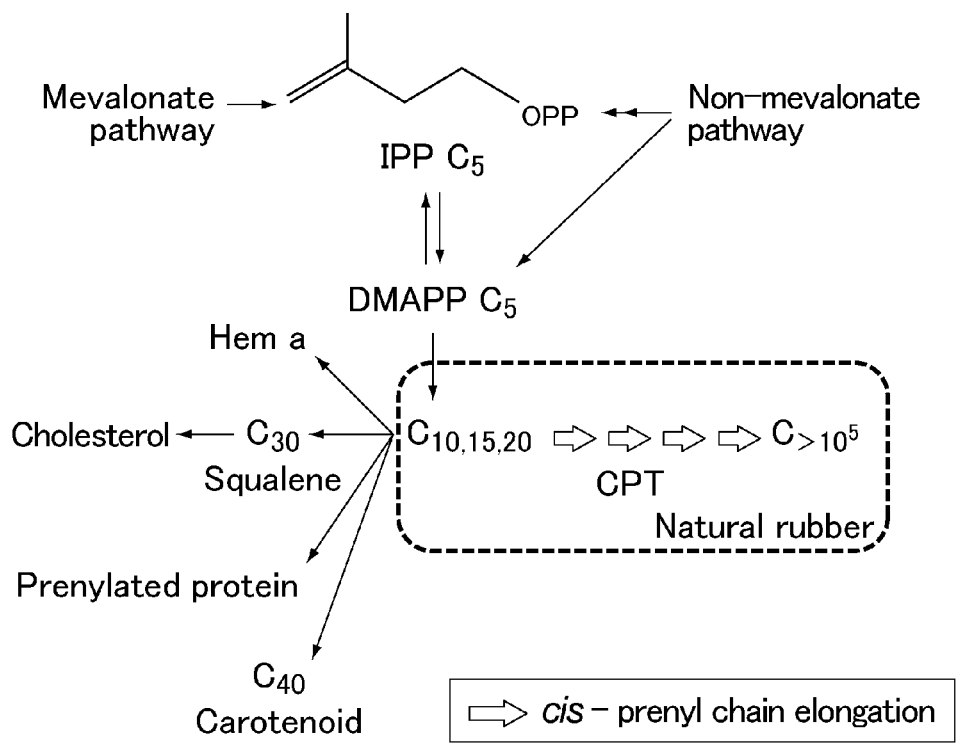
FIG. 2 is a schematic diagram showing part of a polyisoprenoid biosynthesis pathway.

Herein, the cis-prenyltransferase (CPT) family protein refers to an enzyme that catalyzes a reaction of cis-chain elongation of an isoprenoid compound. Specifically, in plants, for example, polyisoprenoids are biosynthesized via polyisoprenoid biosynthesis pathways as shown in FIG. 2, in which the CPT family proteins are considered to be enzymes that catalyze the reaction enclosed by the dotted frame in FIG. 2. The CPT family proteins are characterized by having an amino acid sequence contained in the cis-IPPS domain (NCBI accession No. cd00475). Examples of such CPT family proteins include CPT from *Hevea brasiliensis* (HRT1, HRT2, CPT3-5), AtCPT1-9 from *Arabidopsis thaliana*, CPT1-3 from lettuce, CPT1-3 from *Taraxacum koksaghyz*, and undecaprenyl pyrophosphate synthase (UPPS) from *E. coli*.

Herein, the isoprenoid compound refers to a compound containing an isoprene unit ($C_5H_8$). Also, the cis isoprenoid refers to a compound including an isoprenoid compound in which isoprene units are cis-bonded, and examples include cis-farnesyl diphosphate, undecaprenyl diphosphate, natural rubber, and the like.

The Nogo-B receptor (NgBR) family protein refers to a protein having the functions of binding to a membrane via one or more transmembrane domains on the N-terminal side of the protein, and interacting with CPT family proteins or other proteins on the C-terminal side thereof, and assists the function of the CPT family proteins by holding the CPT family proteins on the membrane. The NgBR family proteins are characterized by having a transmembrane domain on the N-terminal side, and further having an amino acid sequence contained in the cis-IPPS superfamily domain (NCBI accession No. COG0020) on the C-terminal side. Examples of such NgBR family proteins include NgBR from *Hevea brasiliensis* (HRTBP), LEW1 from *Arabidopsis thaliana*, LsCPTL1-2 from lettuce, and TbRTA from *Taraxacum*.

The rubber elongation factor (REF) family protein refers to a rubber particle-associated protein that is bound to rubber particles in the latex of rubber-producing plants such as *Hevea brasiliensis*, and contributes to stabilization of the rubber particles. The REF family proteins are characterized by having an amino acid sequence contained in the REF superfamily domain (NCBI accession No. pfam05755). Examples of such REF family proteins include REF, small rubber particle protein (SRPP) and the like.

Specific examples of the CPT family protein include the following [1]:

[1] a protein having the amino acid sequence of SEQ ID NO:2.

It is known that proteins having one or more amino acid substitutions, deletions, insertions, or additions relative to the original amino acid sequence can have the inherent function. Thus, specific examples of the CPT family protein also include the following [2]:

[2] a protein having an amino acid sequence containing one or more amino acid substitutions, deletions, insertions and/or additions relative to the amino acid sequence of SEQ ID NO:2, and having an enzyme activity that catalyzes a reaction of cis-chain elongation of an isoprenoid compound.

In order to preserve the function of the CPT family protein, it preferably has an amino acid sequence containing one or more, more preferably 1-58, still more preferably 1-44, further more preferably 1-29, particularly preferably 1-15, most preferably 1-6, yet most preferably 1-3 amino acid substitutions, deletions, insertions and/or additions relative to the amino acid sequence of SEQ ID NO:2.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

It is also known that proteins with amino acid sequences having high sequence identity with the original amino acid sequence can also have similar function. Thus, specific examples of the CPT family protein also include the following [3]:

[3] a protein having an amino acid sequence having at least 80% sequence identity with the amino acid sequence of SEQ ID NO:2, and having an enzyme activity that catalyzes a reaction of cis-chain elongation of an isoprenoid compound.

In order to preserve the function of the CPT family protein, the sequence identity with the amino acid sequence of SEQ ID NO:2 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST® [Pro. Natl. Acad. Sci. USA, 90, 5873 (1993)] developed by Karlin and Altschul or FASTA [Methods Enzymol., 183, 63 (1990)] (all the above documents are incorporated herein by reference).

Whether it is a protein having the above enzyme activity may be determined by conventional techniques, such as by expressing a target protein in a transformant prepared by introducing a gene coding for the target protein into *Escherichia coli* or other host organisms, and determining the presence or absence of the function of the target protein by the corresponding activity measurement method.

Specific examples of the NgBR family protein include the following [4]:

[4] a protein having the amino acid sequence of SEQ ID NO:4.

It is known that proteins having one or more amino acid substitutions, deletions, insertions, or additions relative to the original amino acid sequence can have the inherent function. Thus, specific examples of the NgBR family protein also include the following [5]:

[5] a protein having an amino acid sequence containing one or more amino acid substitutions, deletions, insertions and/or additions relative to the amino acid sequence of SEQ ID NO:4, and having the functions of binding to a membrane via one or more transmembrane domains on the N-terminal side of the protein, and interacting with another protein on the C-terminal side thereof.

In order to preserve the function of the NgBR family protein, it preferably has an amino acid sequence containing one or more, more preferably 1-52, still more preferably 1-39, further more preferably 1-26, particularly preferably 1-13, most preferably 1-6, yet most preferably 1-3 amino acid substitutions, deletions, insertions and/or additions relative to the amino acid sequence of SEQ ID NO:4.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

As described above, it is also known that proteins with amino acid sequences having high sequence identity with the original amino acid sequence can also have similar function. Thus, specific examples of the NgBR family protein also include the following [6]:

[6] a protein having an amino acid sequence having at least 80% sequence identity with the amino acid sequence of SEQ ID NO:4, and having the functions of binding to a membrane via one or more transmembrane domains on the N-terminal side of the protein, and interacting with another protein on the C-terminal side thereof.

In order to preserve the function of the NgBR family protein, the sequence identity with the amino acid sequence of SEQ ID NO:4 is preferably at least 85%, more preferably at least 90%, still more preferably at least 95%, particularly preferably at least 98%, most preferably at least 99%.

Whether it is a NgBR family protein may be determined by conventional techniques, such as by identifying the amino acid sequence and then determining whether it has an amino acid sequence contained in the cis-IPPS superfamily domain (NCBI accession No. COG0020).

Specific examples of the REF family protein include the following [7]:

[7] a protein having the amino acid sequence of SEQ ID NO:6.

It is known that proteins having one or more amino acid substitutions, deletions, insertions, or additions relative to the original amino acid sequence can have the inherent function. Thus, specific examples of the REF family protein also include the following [8]:

[8] a rubber particle-associated protein having an amino acid sequence containing one or more amino acid substitutions, deletions, insertions, and/or additions relative to the amino acid sequence of SEQ ID NO:6, and being bound to rubber particles in latex.

In order to preserve the function of the REF family protein, it preferably has an amino acid sequence containing one more, more preferably 1-28, still more preferably 1-21, further more preferably 1-14, particularly preferably 1-7, most preferably 1-3, yet most preferably one amino acid substitution, deletion, insertion and/or addition relative to the amino acid sequence of SEQ ID NO:6.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

As described above, it is also known that proteins with amino acid sequences having high sequence identity with the original amino acid sequence can also have similar function. Thus, specific examples of the REF family protein also include the following [9]:

[9] a rubber particle-associated protein having an amino acid sequence having at least 80% sequence identity with the amino acid sequence of SEQ ID NO:6, and being bound to rubber particles in latex.

In order to preserve the function of the REF family protein, the sequence identity with the amino acid sequence of SEQ ID NO:6 is preferably at least 85%, more preferably at least 90%, still more preferably at least 95%, particularly preferably at least 98%, most preferably at least 99%.

Whether it is a REF family protein may be determined by conventional techniques, such as by identifying the amino acid sequence and then determining whether it has an amino acid sequence contained in the REF superfamily domain (NCBI accession No. pfam05755).

Specific examples of the gene coding for the CPT family protein include the following [1] and [2]:

[1] a DNA having the nucleotide sequence of SEQ ID NO:1; and

[2] a DNA that hybridizes under stringent conditions with a DNA having a nucleotide sequence complementary to the nucleotide sequence of SEQ ID NO:1, and codes for a protein having an enzyme activity that catalyzes a reaction of cis-chain elongation of an isoprenoid compound.

As used herein, the term "hybridizing" means a process in which a DNA hybridizes with a DNA having a specific nucleotide sequence or a part of the DNA. Accordingly, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases although it may be a DNA of at least 10 bases, preferably of at least 15 bases in length.

Techniques to perform DNA hybridization experiments are well known. The hybridization conditions under which experiments are carried out may be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks (all the above documents are incorporated herein by reference).

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridizing under such stringent conditions may have a nucleotide sequence having at least 80%, preferably at least 90%, more preferably at least 95%, still more preferably at least 98%, particularly preferably at least 99% sequence identity with the nucleotide sequence of SEQ ID NO: 1 as calculated using a program such as BLAST® or FASTA with the above-mentioned parameters.

Whether the DNA that hybridizes under stringent conditions with the aforementioned DNA codes for a protein having a predetermined enzyme activity may be determined by conventional techniques, such as by expressing a target protein in a transformant prepared by introducing a gene coding for the target protein into *Escherichia coli* or other host organisms, and determining the presence or absence of the function of the target protein by the corresponding activity measurement method.

Specific examples of the gene coding for the NgBR family protein include the following [3] and [4]:

[3] a DNA having the nucleotide sequence of SEQ ID NO:3; and

[4] a DNA that hybridizes under stringent conditions with a DNA having a nucleotide sequence complementary to the nucleotide sequence of SEQ ID NO:3, and codes for a protein having the functions of binding to a membrane via one or more transmembrane domains on the N-terminal side of the protein, and interacting with another protein on the C-terminal side thereof.

The term "hybridizing" is as described above. Also, the stringent conditions are as described above.

The DNA capable of hybridizing under such stringent conditions may have a nucleotide sequence having at least 80%, preferably at least 90%, more preferably at least 95%, still more preferably at least 98%, particularly preferably at least 99% sequence identity with the nucleotide sequence of SEQ ID NO: 3 as calculated using a program such as BLAST® or FASTA with the above-mentioned parameters.

Whether the DNA that hybridizes under stringent conditions with the aforementioned DNA codes for a NgBR family protein may be determined by conventional techniques, such as by translating the DNA into an amino acid sequence and then determining whether the amino acid sequence has an amino acid sequence contained in the cis-IPPS superfamily domain (NCBI accession No. COG0020).

Specific examples of the gene coding for the REF family protein include the following [5] and [6]:

[5] a DNA having the nucleotide sequence of SEQ ID NO:5; and

[6] a DNA that hybridizes under stringent conditions with a DNA having a nucleotide sequence complementary to the nucleotide sequence of SEQ ID NO:5, and codes for a rubber particle-associated protein that is bound to rubber particles in latex.

The term "hybridizing" is as described above. Also, the stringent conditions are as described above.

The DNA capable of hybridizing under such stringent conditions may have a nucleotide sequence having at least 80%, preferably at least 90%, more preferably at least 95%, still more preferably at least 98%, particularly preferably at least 99% sequence identity with the nucleotide sequence of SEQ ID NO: 5 as calculated using a program such as BLAST® or FASTA with the above-mentioned parameters.

Whether the DNA that hybridizes under stringent conditions with the aforementioned DNA codes for a REF family protein may be determined by conventional techniques, such as by translating the DNA into an amino acid sequence and then determining whether the amino acid sequence has an amino acid sequence contained in the REF superfamily domain (NCBI accession No. pfam05755).

Also, conventional techniques may be employed to identify the amino acid sequence or the nucleotide sequence of the proteins. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the RACE method or the like is performed to identify the full-length nucleotide sequence or amino acid sequence. The RACE method (rapid amplification of cDNA ends method) refers to a method in which, when the nucleotide sequence of a cDNA is partially known, PCR is performed based on the nucleotide sequence information of such a known region to clone an unknown region extending to the cDNA terminal, and is capable of cloning the full-length cDNA by PCR without preparing a cDNA library.

The degenerate primers may each preferably be prepared from a plant-derived sequence having a highly similar sequence part to the target protein.

If the nucleotide sequence coding for the protein is known, it is possible to identify the full-length nucleotide sequence or amino acid sequence by designing a primer containing an initiation codon and a primer containing a termination codon using the known nucleotide sequence followed by performing RT-PCR using a synthesized cDNA as a template.

In the binding step, another protein may further be bound to the rubber particles as long as the protein expressed by a gene coding for a cis-prenyltransferase (CPT) family protein, the protein expressed by a gene coding for a Nogo-B receptor (NgBR) family protein, and the protein expressed by a gene coding for a rubber elongation factor (REF) family protein are bound to the rubber particles in vitro.

The origin of the other protein is not particularly limited, but preferably it is derived from any of the plants described above, more preferably at least one selected from the group consisting of plants of the genera Hevea, Sonchus, Taraxacum, and Parthenium. Among these, it is still more preferably derived from at least one species of plant selected from the group consisting of Hevea brasiliensis, Sonchus oleraceus, Parthenium argentatum, and Taraxacum kok-saghyz, particularly preferably Hevea brasiliensis.

The other protein may be any protein without any limitations, but for purposes of enhancing the rubber synthesis activity of the rubber particles, it is preferably a protein that inherently exists on rubber particles in rubber-producing plants. The protein that exists on rubber particles may be a protein that binds to a large part of the membrane surface of rubber particles, or a protein that is inserted into and bound to the membrane of rubber particles, or a protein that forms a complex with another protein bound to the membrane so as to be present on the membrane surface.

Examples of the protein that inherently exists on rubber particles in rubber-producing plants include β-1,3-glucanase, and Hevein.

The binding step may be carried out by any method that binds the CPT family protein, NgBR family protein, and REF family protein to rubber particles in vitro, such as, for example, by performing protein synthesis in the presence of both rubber particles and a cell-free protein synthesis solution containing an mRNA coding for the CPT family protein, an mRNA coding for the NgBR family protein, and an mRNA coding for the REF family protein to bind the CPT family protein, the NgBR family protein, and the REF family protein to the rubber particles.

The binding step preferably includes performing protein synthesis in the presence of both rubber particles and a cell-free protein synthesis solution containing an mRNA coding for a CPT family protein, an mRNA coding for a NgBR family protein, and an mRNA coding for a REF family protein to bind the CPT family protein, the NgBR family protein, and the REF family protein to the rubber particles, among other methods.

In other words, rubber particles bound to a CPT family protein, a NgBR family protein, and a REF family protein are preferably obtained by performing protein synthesis in the presence of both rubber particles and a cell-free protein synthesis solution containing mRNAs coding for the CPT family protein, the NgBR family protein, and the REF family protein, or, more specifically, using a mixture of rubber particles with a cell-free protein synthesis solution containing mRNAs coding for the CPT family protein, the NgBR family protein, and the REF family protein.

Since liposomes are produced artificially as lipid bilayer membranes consisting of phospholipids, glyceroglycolipids, cholesterol and other components, the produced liposomes have no proteins bound to their surface. On the other hand, although rubber particles harvested from the latex of rubber-producing plants are also coated with a lipid membrane, the membrane of rubber particles is a naturally derived membrane in which proteins that have been synthesized in the plants are already bound to the surface of the membrane. Hence, binding of an additional protein to rubber particles that are already bound to and coated with proteins is expected to be more difficult than binding to liposomes not bound to any protein. There is also concern that the proteins already bound to rubber particles could inhibit cell-free protein synthesis. For these reasons, difficulties have been anticipated in achieving cell-free protein synthesis in the presence of rubber particles. Under such circumstances, the present inventors have first discovered that rubber particles bound to a CPT family protein, a NgBR family protein, and a REF family protein can be produced by performing cell-free synthesis of the CPT family protein, the NgBR family protein, and the REF family protein in the presence of rubber particles, which had never been attempted in the past.

The protein synthesis in the presence of both rubber particles and a cell-free protein synthesis solution containing mRNAs coding for a CPT family protein, a NgBR family protein, and a REF family protein is namely the synthesis of a CPT family protein, a NgBR family protein, and a REF family protein by cell-free protein synthesis, and the synthesized CPT family protein, NgBR family protein, and REF family protein maintain biological functions (the native state). As the cell-free protein synthesis is performed in the presence of rubber particles, the synthesized CPT family protein, NgBR family protein, and REF family protein in the native state can be bound to the rubber particles.

Herein, binding of a CPT family protein, a NgBR family protein, and a REF family protein to rubber particles by protein synthesis in the presence of both the cell-free protein synthesis solution and the rubber particles means that, for example, all or part of the CPT family protein, NgBR family protein, and REF family protein synthesized by the protein synthesis is incorporated into the rubber particles, or inserted into the membrane structure of the rubber particles. It is not limited to these embodiments and also includes embodiments in which, for example, the proteins are localized on the surface or inside of the rubber particles. Moreover, the concept of binding to rubber particle also includes embodiments in which the proteins form a complex with another protein bound to the rubber particles as described above, so as to be present in the form of the complex on the rubber particles.

The mRNAs coding for a CPT family protein, a NgBR family protein, and a REF family protein serve as translation templates that can be translated to synthesize the CPT family protein, NgBR family protein, and REF family protein, respectively.

The origins of the mRNAs coding for a CPT family protein, a NgBR family protein, and a REF family protein are not particularly limited, but preferably they are each derived from any of the plants described above, more preferably at least one selected from the group consisting of plants of the genera *Hevea, Sonchus, Taraxacum,* and *Parthenium*. Among these, they are each still more preferably derived from at least one species of plant selected from the group consisting of *Hevea brasiliensis, Sonchus oleraceus, Parthenium argentatum,* and *Taraxacum kok-saghyz*, particularly preferably *Hevea brasiliensis*.

The methods for preparing the mRNAs coding for a CPT family protein, a NgBR family protein, and a REF family protein are not particularly limited as long as the prepared mRNAs serve as translation templates that can be translated to synthesize the CPT family protein, NgBR family protein, and REF family protein. For example, the mRNAs may be prepared by extracting total RNA from the latex of a rubber-producing plant by, for example, the hot phenol method, synthesizing cDNA from the total RNA, obtaining a DNA fragment of a gene coding for a CPT family protein, NgBR family protein, or REF family protein using primers prepared based on the nucleotide sequence data of the gene coding for a CPT family protein, NgBR family protein, or REF family protein, and performing an ordinary in vitro transcription of the DNA fragment.

As long as the cell-free protein synthesis solution contains the mRNAs coding for a CPT family protein, a NgBR family protein, and a REF family protein, it may contain a mRNA coding for another protein.

The mRNA coding for another protein may be an mRNA that can be translated to express the other protein. The other protein may be as described above.

In the binding step in the first invention, cell-free synthesis of a CPT family protein, a NgBR family protein, and a REF family protein is preferably performed in the presence of rubber particles. This cell-free protein synthesis may be carried out by methods similar to conventional methods using the cell-free protein synthesis solution. Commonly used cell-free protein synthesis techniques may be employed for the cell-free protein synthesis system, such as a rapid translation system RTS500 (Roche Diagnostics); and wheat germ extracts prepared in accordance with Proc. Natl. Acad. Sci. USA, 97:559-564 (2000), JP-A 2000-236896, JP-A 2002-125693 or JP-A 2002-204689, and cell-free protein synthesis systems using the wheat germ extracts (JP-A 2002-204689, Proc. Natl. Acad. Sci. USA, 99:14652-14657 (2002)). All the above documents are incorporated herein by reference. Systems using germ extracts are preferred among these. Thus, in another suitable embodiment of the first invention, the cell-free protein synthesis solution contains a germ extract.

The source of the germ extract is not particularly limited. From the standpoint of translation efficiency, it is preferred to use a plant-derived germ extract when a plant protein is synthesized by cell-free protein synthesis. It is particularly preferred to use a wheat-derived germ extract. Thus, in another suitable embodiment of the first invention, the germ extract is derived from wheat.

The method for preparing the germ extract is not particularly limited, and may be carried out conventionally, as described in, for example, JP-A 2005-218357, incorporated herein by reference.

The cell-free protein synthesis solution preferably further contains a cyclic nucleoside monophosphate derivative or a salt thereof (hereinafter, also referred to simply as "activity enhancer"). Protein synthesis activity can be further enhanced by the inclusion of the activity enhancer.

The cyclic nucleoside monophosphate derivative or salt thereof is not particularly limited as long as it can enhance cell-free protein synthesis activity, and examples include adenosine-3',5'-cyclic monophosphoric acid and its salts; adenosine-3',5'-cyclic monophosphorothioic acid (Sp-isomer) and its salts; adenosine-3',5'-cyclic monophosphorothioic acid (Rp-isomer) and its salts; guanosine-3',5'-cyclic monophosphoric acid and its salts; guanosine-3',5'-cyclic monophosphorothioic acid (Sp-isomer) and its salts; guanosine-3',5'-cyclic monophosphorothioic acid (Rp-isomer) and its salts; 8-bromoadenosine-3',5'-cyclic monophosphoric acid (bromo-cAMP) and its salts; 8-(4-chlorophenylthio)adenosine-3',5'-cyclic monophosphoric acid (chlorophenylthio-cAMP) and its salts; 5,6-dichloro-1-β-D-ribofuranosylbenzimidazole adenosine-3',5'-cyclic monophosphoric acid (dichlororibofuranosylbenzimidazole cAMP) and its salts; adenosine-2',5'-cyclic monophosphoric acid and its salts; adenosine-2',5'-cyclic monophosphorothioic acid (Sp-isomer) and its salts; adenosine-2',5'-cyclic monophosphorothioic acid (Rp-isomer) and its salts; guanosine-2',5'-cyclic monophosphoric acid and its salts; guanosine-2',5'-cyclic monophosphorothioic acid (Sp-isomer) and its salts; and guanosine-2',5'-cyclic monophosphorothioic acid (Rp-isomer) and its salts.

The base that forms a salt with the cyclic nucleoside monophosphate derivative is not particularly limited as long as it is biochemically acceptable and forms a salt with the derivative. Preferred are, for example, alkali metal atoms such as sodium or potassium, and organic bases such as Tris-hydroxyaminomethane, among others.

Of these activity enhancers, adenosine-3',5'-cyclic monophosphoric acid or adenosine-3',5'-cyclic monophosphate sodium is particularly preferred. These activity enhancers may be used alone or in combinations of two or more.

The activity enhancer may be incorporated into the cell-free protein synthesis solution in advance. If the activity enhancer is unstable in the solution, it is preferably added during the protein synthesis reaction performed in the presence of both the cell-free protein synthesis solution and rubber particles.

The amount of the activity enhancer added is not particularly limited as long as the activity enhancer is at a concentration that can activate (increase) the protein synthesis reaction in the cell-free protein synthesis solution. Specifically, the final concentration in the reaction system may usually be at least 0.1 millimoles/liter. The lower limit of the concentration is preferably 0.2 millimoles/liter, more preferably 0.4 millimoles/liter, particularly preferably 0.8 millimoles/liter, while the upper limit of the concentration is preferably 24 millimoles/liter, more preferably 6.4 millimoles/liter, particularly preferably 3.2 millimoles/liter.

When adding the activity enhancer to the cell-free protein synthesis solution, the temperature of the cell-free protein synthesis solution is not particularly limited, but is preferably 0° C. to 30° C., more preferably 10° C. to 26° C.

In addition to the mRNAs (translation templates) coding for a CPT family protein, a NgBR family protein, and a REF family protein, the cell-free protein synthesis solution also contains ATP, GTP, creatine phosphate, creatine kinase, L-amino acids, potassium ions, magnesium ions and other components required for protein synthesis, and optionally an activity enhancer. Such a cell-free protein synthesis solution can serve as a cell-free protein synthesis reaction system.

Since the germ extract prepared by the method described in JP-A 2005-218357 contains tRNA in an amount necessary for protein synthesis reaction, addition of separately prepared tRNA is not required when the germ extract prepared by the above method is used in the cell-free protein synthesis solution. In other words, tRNA may be added to the cell-free protein synthesis solution as necessary.

The binding step in the first invention preferably includes performing protein synthesis in the presence of both rubber particles and a cell-free protein synthesis solution containing mRNAs coding for a CPT family protein, a NgBR family protein, and a REF family protein. Specifically, this can be accomplished by adding rubber particles to the cell-free protein synthesis solution at a suitable point either before or after protein synthesis, preferably before protein synthesis.

The rubber particles are preferably present in the cell-free protein synthesis solution at a concentration of 5 to 50 g/L. In other words, 5 to 50 g of rubber particles are preferably present in 1 L of the cell-free protein synthesis solution. When the concentration of rubber particles present in the cell-free protein synthesis solution is less than 5 g/L, a rubber layer may not be formed by separation treatment (e.g. ultracentrifugation) for collecting the rubber particles bound to the synthesized CPT family protein, NgBR family protein, and REF family protein, and therefore it may be difficult to collect the rubber particles bound to the synthesized CPT family protein, NgBR family protein, and REF family protein. When the concentration of rubber particles present in the cell-free protein synthesis solution exceeds 50 g/L, the rubber particles may coagulate, so that the synthesized CPT family protein, NgBR family protein, and REF family protein may fail to bind well to the rubber particles. The concentration of rubber particles is more preferably 10 to 40 g/L, still more preferably 15 to 35 g/L, particularly preferably 15 to 30 g/L.

In the protein synthesis in the presence of both rubber particles and the cell-free protein synthesis solution, rubber particles may be added as appropriate as the reaction progresses. The cell-free protein synthesis solution and rubber particles are preferably present together during the period when the cell-free protein synthesis system is active, such as 3 to 48 hours, preferably 3 to 30 hours, more preferably 3 to 24 hours after the addition of rubber particles to the cell-free protein synthesis solution.

The rubber particles do not have to be subjected to any treatment, e.g. pretreatment, before use in the binding step in the first invention, preferably before being combined with the cell-free protein synthesis solution. However, proteins may be removed from the rubber particles with a surfactant beforehand to increase the proportions of the CPT family protein, NgBR family protein, and REF family protein desired to be bound by the method of the first invention, among the proteins present on the rubber particles. Thus, in another suitable embodiment of the first invention, the rubber particles used in the first invention are washed with a surfactant before use in the binding step in the first invention, preferably before being combined with the cell-free protein synthesis solution.

The surfactant is not particularly limited, and examples include nonionic surfactants and amphoteric surfactants. Nonionic surfactants and amphoteric surfactants, among others, are suitable because they have only a little denaturing effect on the proteins on the membrane, and amphoteric surfactants are especially suitable. Thus, in another suitable embodiment of the first invention, the surfactant is an amphoteric surfactant.

These surfactants may be used alone or in combinations of two or more.

Examples of nonionic surfactants include polyoxyalkylene ether nonionic surfactants, polyoxyalkylene ester nonionic surfactants, polyvalent alcohol fatty acid ester nonionic surfactants, sugar fatty acid ester nonionic surfactants, alkyl polyglycoside nonionic surfactants, and polyoxyalkylene polyglucoside nonionic surfactants; and polyoxyalkylene alkylamines and alkyl alkanolamides.

Of these, polyoxyalkylene ether nonionic surfactants or polyvalent alcohol fatty acid ester nonionic surfactants are preferred.

Examples of polyoxyalkylene ether nonionic surfactants include polyoxyalkylene alkyl ethers, polyoxyalkylene alkylphenyl ethers, polyoxyalkylene polyol alkyl ethers, and polyoxyalkylene mono-, di- or tristyryl phenyl ethers. Among these, polyoxyalkylene alkylphenyl ethers are suitable. The polyol is preferably a $C_{2-12}$ polyvalent alcohol, such as ethylene glycol, propylene glycol, glycerin, sorbitol, glucose, sucrose, pentaerythritol, or sorbitan.

Examples of polyoxyalkylene ester nonionic surfactants include polyoxyalkylene fatty acid esters and polyoxyalkylene alkyl rosin acid esters.

Examples of polyvalent alcohol fatty acid ester nonionic surfactants include fatty acid esters of $C_{2-12}$ polyvalent alcohols and fatty acid esters of polyoxyalkylene polyvalent alcohols. More specific examples include sorbitol fatty acid esters, sorbitan fatty acid esters, glycerin fatty acid esters, polyglycerin fatty acid esters, and pentaerythritol fatty acid esters, as well as polyalkylene oxide adducts of the foregoing (e.g. polyoxyalkylene sorbitan fatty acid esters, polyoxyalkylene glycerin fatty acid esters). Among these, sorbitan fatty acid esters are suitable.

Examples of sugar fatty acid ester nonionic surfactants include fatty acid esters of sucrose, glucose, maltose, fructose and polysaccharides, as well as polyalkylene oxide adducts of the foregoing.

Examples of alkyl polyglycoside nonionic surfactants include those having glucose, maltose, fructose, sucrose and the like as glycosides, such as alkyl glucosides, alkyl polyglucosides, polyoxyalkylene alkyl glucosides, and polyoxyalkylene alkyl polyglucosides, as well as fatty acid esters of the foregoing. Polyalkylene oxide adducts of any of the foregoing may also be used.

Examples of the alkyl groups in these nonionic surfactants include $C_{4-20}$ linear or branched, saturated or unsaturated alkyl groups. The polyoxyalkylene groups may have $C_{2-4}$ alkylene groups, and may have about 1-50 moles of added ethylene oxide, for example. Examples of the fatty acids include $C_{4-20}$ linear or branched, saturated or unsaturated fatty acids.

Of the nonionic surfactants, polyoxyethylene (10) octylphenyl ether (Triton X-100) or sorbitan monolaurate (Span 20) is particularly preferred for their ability to moderately remove membrane-bound proteins while keeping the membrane of rubber particle stable and, further, having only a little denaturing effect on the proteins.

Examples of amphoteric surfactants include zwitterionic surfactants such as quaternary ammonium group/sulfonate group ($-SO_3H$) surfactants, water-soluble quaternary ammonium group/phosphate group surfactants, water-insoluble quaternary ammonium group/phosphate group surfactants, and quaternary ammonium group/carboxyl group surfactants. The acid groups in these zwitterionic surfactants may be salts.

In particular, the zwitterionic surfactant preferably has both positive and negative charges in a molecule, and the acid dissociation constant (pKa) of the acid group is preferably 5 or less, more preferably 4 or less, still more preferably 3 or less.

Specific examples of the amphoteric surfactant include ammonium sulfobetaines such as 3-[3-cholamidopropyl)dimethylamino]-2-hydroxy-1-propanesulfonate (CHAPSO), 3-[3-cholamidopropyl)-dimethylamino]-propanesulfonate (CHAPS), N,N-bis(3-D-gluconamidopropyl)-cholamide, n-octadecyl-N,N'-dimethyl-3-amino-1-propanesulfonate, n-decyl-N,N'-dimethyl-3-amino-1-propanesulfonate, n-dodecyl-N,N'-dimethyl-3-amino-1-propanesulfonate, n-tetradecyl-N,N'-dimethyl-3-amino-1-propanesulfonate {Zwittergent™-3-14}, n-hexadecyl-N,N'-dimethyl-3-amino-1-propanesulfonate, and n-octadecyl-N,N'-dimethyl-3-amino-1-propanesulfonate; phosphocholines such as n-octylphosphocholine, n-nonylphosphocholine, n-decylphosphocholine, n-dodecylphosphocholine, n-tetradecylphosphocholine, and n-hexadecylphosphocholine; and phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, and dilinoleoyl phosphatidylcholine. Of these, 3-[(3-cholamidopropyl)dimethylamino]-propanesulfonate (CHAPS) is particularly preferred for its ability to moderately remove proteins while keeping the membrane of rubber particles stable.

The concentration of the surfactant for the treatment is preferably within three times the critical micelle concentration (CMC) of the surfactant used. The membrane stability of the rubber particles may be reduced if they are treated with the surfactant at a concentration exceeding three times the critical micelle concentration. The concentration is more preferably within 2.5 times, still more preferably within 2.0 times the CMC. The lower limit of the concentration is preferably 0.05 times or more, more preferably 0.1 times or more, still more preferably 0.3 times or more the CMC.

Examples of reaction systems or apparatuses that can be used in the cell-free protein synthesis include a batch method (Pratt, J. M. et al., Transcription and Translation, Hames, 179-209, B. D. & Higgins, S. J., eds, IRL Press, Oxford (1984)), a continuous cell-free protein synthesis system in which amino acids, energy sources and the like are supplied continuously to the reaction system (Spirin, A. S. et al., Science, 242, 1162-1164 (1988)), a dialysis method (Kigawa et al., 21st Annual Meeting of the Molecular Biology Society of Japan, WID 6) and an overlay method (instruction manual of PROTEIOS™ wheat germ cell-free protein synthesis core kit, Toyobo Co., Ltd.). All the above documents are incorporated herein by reference. Another method may be to supply template RNA, amino acids, energy sources and the like as necessary to the protein synthesis reaction system, and discharge the synthesis product or decomposition product as required.

Among these, the overlay method has the advantage of easy operation, but unfortunately the rubber particles disperse in the reaction solution and thus are difficult to efficiently bind to the synthesized CPT family protein, NgBR family protein, and REF family protein, while, in the dialysis method, since the amino acids used as raw materials of the CPT family protein, NgBR family protein, and REF family protein to be synthesized can pass through the dialysis membrane but the rubber particles cannot pass therethrough, the dispersal of the rubber particles can be prevented, and thus it is possible to efficiently bind the synthesized CPT family protein, NgBR family protein, and REF family protein to the rubber particles. Accordingly, the dialysis method is preferred.

The dialysis method refers to a method in which protein synthesis is carried out using the reaction solution for the cell-free protein synthesis as an inner dialysis solution, and an apparatus in which the inner dialysis solution is separated from an outer dialysis solution by a dialysis membrane capable of mass transfer. Specifically, for example, a translation template is added to the synthesis reaction solution excluding the translation template, optionally after pre-incubation for an appropriate amount of time, and then the solution is put in a suitable dialysis container as the inner reaction solution. Examples of the dialysis container include containers with a dialysis membrane attached to the bottom (e.g. Dialysis Cup 12000 available from Daiichi Kagaku) and dialysis tubes (e.g. 12000 available from Sanko Junyaku Co., Ltd.). The dialysis membrane used has a molecular weight cutoff of 10,000 daltons or more, preferably about 12,000 daltons.

The outer dialysis solution used is a buffer containing amino acids. The dialysis efficiency can be increased by replacing the outer dialysis solution with a fresh solution when the reaction speed declines. The reaction temperature and time are selected appropriately according to the protein synthesis system used. For example, in the case of a system using a wheat-derived germ extract, the reaction may be carried out usually at 10° C. to 40° C., preferably 18° C. to 30° C., more preferably 20° C. to 26° C., for 10 minutes to 48 hours, preferably for 10 minutes to 30 hours, more preferably for 10 minutes to 24 hours.

Since the mRNAs coding for a CPT family protein, a NgBR family protein, and a REF family protein contained in the cell-free protein synthesis solution are easily broken down, the mRNAs may be additionally added as appropriate during the protein synthesis reaction to make the protein synthesis more efficient. Thus, in another suitable embodiment of the first invention, the mRNAs coding for a CPT family protein, a NgBR family protein, and a REF family protein are additionally added during the protein synthesis reaction.

The addition time, the number of additions, the addition amount and other conditions of the mRNAs are not particularly limited, and may be selected appropriately.

In the production method of the first invention, a step of collecting the rubber particles may optionally be performed after the step of binding a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein to rubber particles in vitro.

The rubber particle collection step may be carried out by any method, provided that the rubber particles can be collected. It may be carried out by conventional methods for collecting rubber particles. Specific examples include methods using centrifugation. When the rubber particles are collected by the centrifugation, the centrifugal force, centrifugation time, and centrifugation temperature may be selected appropriately so as to allow the rubber particles to be collected. For example, the centrifugal force during the centrifugation is preferably 15000×g or more, more preferably 20000×g or more, still more preferably 25000×g or more. Since increasing the centrifugal force too much is not expected to produce a correspondingly high separation effect, the upper limit of the centrifugal force is preferably 50000×g or less, more preferably 45000×g or less. The centrifugation time is preferably at least 20 minutes, more preferably at least 30 minutes, still more preferably at least 40 minutes. Since increasing the centrifugation time too much is not expected to produce a correspondingly high separation effect, the upper limit of the centrifugation time is preferably 120 minutes or less, more preferably 90 minutes or less.

From the standpoint of maintaining the protein activity of the CPT family protein, NgBR family protein, and REF family protein bound to the rubber particles, the centrifugation temperature is preferably 0° C. to 10° C., more preferably 2° C. to 8° C., particularly preferably 4° C.

For example, when the cell-free protein synthesis is performed, the rubber particles and the cell-free protein synthesis solution are separated into the upper layer and the lower layer, respectively, by the centrifugation. The cell-free protein synthesis solution as the lower layer may then be removed to collect the rubber particles bound to the CPT family protein, NgBR family protein, and REF family protein. The collected rubber particles may be re-suspended in a suitable buffer with a neutral pH for storage.

Since the CPT family protein, NgBR family protein, and REF family protein to be bound to the rubber particles are proteins that inherently exist on rubber particles in rubber-producing plants, the rubber particles collected by the rubber particle collection step can be used in the same way as usual natural rubber without the need for further special treatment.

Moreover, the polyisoprenoid obtained by the method for producing a polyisoprenoid of the first invention can be collected by subjecting the rubber particles to the following solidification step.

The method for solidification is not particularly limited, and examples include a method of adding the rubber particles to a solvent that does not dissolve the polyisoprenoid (natural rubber), such as ethanol, methanol or acetone; and a method of adding an acid to the rubber particles. Rubber (natural rubber) can be recovered as solids from the rubber particles by the solidification step. The obtained rubber (natural rubber) may be dried as necessary before use.

As described above, according to the first invention, the rubber synthesis activity of rubber particles can be enhanced by binding a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein to rubber particles in vitro. Thus, it is possible to produce rubber (one example of polyisoprenoids) more efficiently in reaction vessels (e.g. test tubes, industrial plants).

Thus, another aspect of the first invention relates to a method for synthesizing a polyisoprenoid, which includes a step of binding a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein to rubber particles in vitro, for example in a reaction vessel (e.g. a test tube or industrial plant).

The step of binding a protein expressed by a gene coding for a cis-prenyltransferase (CPT) family protein, a protein expressed by a gene coding for a Nogo-B receptor (NgBR) family protein, and a protein expressed by a gene coding for a rubber elongation factor (REF) family protein to rubber particles in vitro is as described above.

Herein, the term "polyisoprenoid" is a collective term for polymers composed of isoprene units ($C_5H_8$). Examples of the polyisoprenoid include sesterterpenes ($C_{25}$), triterpenes ($C_{30}$), tetraterpenes ($C_{40}$), natural rubber, and other polymers. Herein, the term "isoprenoid" refers to a compound having isoprene units ($C_5H_8$), and conceptually includes polyisoprenoids.

(Method for Producing Rubber Product)

The method for producing a rubber product of the first invention includes the steps of: kneading a polyisoprenoid produced by the method for producing a polyisoprenoid of the first invention with an additive to obtain a kneaded mixture; forming a raw rubber product from the kneaded mixture; and vulcanizing the raw rubber product.

The rubber product is not particularly limited as long as it is a rubber product that can be produced from rubber, preferably natural rubber, and examples include pneumatic tires, rubber rollers, rubber fenders, gloves, and medical rubber tubes.

When the rubber product is a pneumatic tire, or in other words when the method for producing a rubber product of the first invention is a method for producing a pneumatic tire, the raw rubber product forming step corresponds to a green tire building step in which a green tire is built from the kneaded mixture, and the vulcanization step corresponds to a vulcanization step in which the green tire is vulcanized. Thus, the method for producing a pneumatic tire of the first invention includes the steps of: kneading a polyisoprenoid produced by the method for producing a polyisoprenoid with an additive to obtain a kneaded mixture; building a green (or raw) tire from the kneaded mixture; and vulcanizing the green tire.

<Kneading Step>

In the kneading step, the polyisoprenoid produced by the method for producing a polyisoprenoid is kneaded with an additive to obtain a kneaded mixture.

The additive is not particularly limited, and additives used in production of rubber products may be used. For example, when the rubber product is a pneumatic tire, examples include rubber components other than the polyisoprenoid, reinforcing fillers such as carbon black, silica, calcium carbonate, alumina, clay, or talc, silane coupling agents, zinc oxide, stearic acid, processing aids, various antioxidants, softeners such as oil, wax, vulcanizing agents such as sulfur, and vulcanization accelerators.

The kneading in the kneading step may be carried out using an open roll mill, a Banbury mixer, an internal mixer, or other rubber kneading machines.

<Raw Rubber Product Forming Step (Green Tire Building Step for Tire)>

In the raw rubber product forming step, a raw rubber product (green tire for tire) is formed (or built) from the kneaded mixture obtained in the kneading step.

The method for forming a raw rubber product is not particularly limited, and methods used to form raw rubber products may be used appropriately. For example, when the rubber product is a pneumatic tire, the kneaded mixture obtained in the kneading step may be extruded according to the shape of a tire component and then formed by a usual method on a tire building machine and assembled with other tire components to build a green tire (unvulcanized tire).

<Vulcanization Step>

In the vulcanization step, the raw rubber product obtained in the raw rubber product forming step is vulcanized to obtain a rubber product.

The method for vulcanizing the raw rubber product is not particularly limited, and methods used to vulcanize raw rubber products may be used appropriately. For example, when the rubber product is a pneumatic tire, the green tire (unvulcanized tire) obtained in the green tire building step may be vulcanized by heating and pressing in a vulcanizer to obtain a pneumatic tire.

Second Invention

The method for producing a polyisoprenoid of the second invention includes producing a polyisoprenoid in a transformed plant produced by introducing a gene coding for a cis-prenyltransferase (CPT) family protein, a gene coding for a Nogo-B receptor (NgBR) family protein, and a gene coding for a rubber elongation factor (REF) family protein into a plant to allow the plant to express the CPT family protein, the NgBR family protein, and the REF family protein.

The inventors were the first to discover that the rubber synthesis of rubber particles is activated by binding a CPT family protein, a NgBR family protein, and a REF family protein to rubber particles in vitro. Based on this finding, it is expected that rubber synthesis activity can be enhanced by co-expressing a CPT family protein, a NgBR family protein, and a REF family protein in a plant. Thus, the use of a transformed plant engineered to co-express a CPT family protein, a NgBR family protein, and a REF family protein in polyisoprenoid production is expected to result in increased polyisoprenoid production.

It is also considered that rubber synthesis activity can be improved in transformed plants produced by introducing a gene coding for a CPT family protein, a gene coding for a NgBR family protein, and a gene coding for a REF family protein individually into respective plants. However, the co-expression of these three genes is considered to provide a further synergistic effect. For example, when the CPT family protein is expressed alone, if the amount of the NgBR family protein expressed is low, the CPT family protein may fail to bind to rubber particles and, therefore, fail to function. Also, when the NgBR family protein is expressed alone, if the amount of the CPT family protein (synthase) expressed is low, the rubber synthesis activity may not be sufficiently improved. In contrast, co-expression of the CPT family protein and NgBR family protein is considered to lead to enhanced rubber synthesis activity, and when the REF family protein is further expressed, it is considered that the rubber particles that are expected to have enhanced rubber synthesis activity due to the co-expression of the CPT family protein and NgBR family protein can stably accumulate in the plant. Thus, it is expected that rubber synthesis activity can be significantly enhanced by co-expressing the CPT family protein, NgBR family protein, and REF family protein in a plant.

Since the method for producing a polyisoprenoid of the second invention uses a transformed plant having specific genes introduced therein, unlike conventional methods involving chemical administration, continuous effects can be expected without subsequent continuing treatment because once the genes have been introduced, the effects of the gene introduction are obtained through inherent biological mechanisms.

The origins of the gene coding for a cis-prenyltransferase (CPT) family protein, the gene coding for a Nogo-B receptor (NgBR) family protein, and the gene coding for a rubber elongation factor (REF) family protein are not particularly limited, but preferably they are each derived from any of the plants described above, more preferably at least one selected from the group consisting of plants of the genera *Hevea, Sonchus, Taraxacum*, and *Parthenium*. Among these, they are each still more preferably derived from at least one species of plant selected from the group consisting of *Hevea brasiliensis, Sonchus oleraceus, Parthenium argentatum*, and *Taraxacum kok-saghyz*, particularly preferably *Hevea brasiliensis*. Most preferably, they are all derived from *Hevea brasiliensis*. Whatever their origins, the gene coding for a CPT family protein, the gene coding for a NgBR family protein, and the gene coding for a REF family protein are preferably derived from the species of plant into which they are to be introduced.

The gene coding for a cis-prenyltransferase (CPT) family protein, the gene coding for a Nogo-B receptor (NgBR) family protein, and the gene coding for a rubber elongation factor (REF) family protein, and the CPT family protein, the NgBR family protein, and the REF family protein used in the second invention are as described above in connection with the first invention.

In the method for producing a polyisoprenoid of the second invention, a gene coding for another protein may further be introduced into the plant as long as the gene coding for a cis-prenyltransferase (CPT) family protein, the gene coding for a Nogo-B receptor (NgBR) family protein, and the gene coding for a rubber elongation factor (REF) family protein are introduced into the plant.

The gene coding for another protein may be as described above in connection with the first invention.

By introducing the gene coding for a cis-prenyltransferase (CPT) family protein, the gene coding for a Nogo-B receptor (NgBR) family protein, and the gene coding for a rubber elongation factor (REF) family protein into a plant, a plant (transformed plant) is produced which has been transformed to express the CPT family protein, the NgBR family protein, and the REF family protein. Since the CPT family protein, NgBR family protein, and REF family protein are co-expressed in the transformed plant, the activity of the CPT family protein is expected to be stabilized and enhanced. Therefore, it is expected that the transformed plant engineered to co-express the CPT family protein, NgBR family protein, and REF family protein exhibits continuously enhanced rubber synthesis activity, and the use of such a transformed plant in polyisoprenoid production can suitably result in an increase in polyisoprenoid production.

The method for preparing the plant transformed to express the CPT family protein, NgBR family protein, and REF family protein (transformed plant) is explained briefly below, but such a transformed plant can be prepared by conventionally known methods.

Specifically, for example, the method for preparing the transformed plant may be carried out as follows: A DNA containing the nucleotide sequence of SEQ ID NO:1, a DNA containing the nucleotide sequence of SEQ ID NO:3, and a DNA containing the nucleotide sequence of SEQ ID NO:5 are inserted downstream of the promoter of a suitable expression vector with suitable restriction enzymes and the like to prepare a recombinant DNA. This recombinant DNA may then be introduced into host plant cells which are compatible with the expression vector, to obtain transformed plant cells. Alternatively, an expression vector in which a DNA containing the nucleotide sequence of SEQ ID NO:1 is inserted downstream of the promoter with suitable restriction enzymes and the like, an expression vector in which a DNA containing the nucleotide sequence of SEQ ID NO:3 is inserted downstream of the promoter with suitable restriction enzymes and the like, and an expression vector in which a DNA containing the nucleotide sequence of SEQ ID NO:5 is inserted downstream of the promoter with suitable restriction enzymes and the like are used to prepare recombinant DNAs, and these recombinant DNAs may then be introduced into host plant cells which are compatible with the expression vectors, to obtain transformed plant cells.

There are no particular restrictions on the plant (host plant cells) into which the recombinant DNA is to be introduced, but since improved polyisoprenoid productivity and increased polyisoprenoid production can be expected in particular when the CPT family protein, NgBR family protein, and REF family protein are expressed in plants capable of polyisoprenoid biosynthesis, the plant is preferably a rubber-producing plant, and the host plant cells are preferably plant cells of a rubber-producing plant. Thus, in another suitable embodiment of the second invention, the plant into which the gene coding for a cis-prenyltransferase (CPT) family protein, the gene coding for a Nogo-B receptor (NgBR) family protein, and the gene coding for a rubber elongation factor (REF) family protein are to be introduced is a polyisoprenoid-producing plant, more preferably at least one species of rubber-producing plant selected from the group consisting of *Hevea brasiliensis, Sonchus oleraceus, Parthenium argentatum*, and *Taraxacum kok-saghyz*, particularly preferably *Hevea brasiliensis*.

The expression vector may be a vector that is capable of autonomous replication in the host plant cells or can be incorporated into the chromosome, and, further, contains a promoter at a position allowing transcription of the recombinant DNA.

Examples of the expression vector include pBI vectors, Ti plasmids, and tobacco mosaic virus vectors.

Any promoter that functions in plant cells can be used as the promoter, and examples include cauliflower mosaic virus (CaMV) 35S promoter, rice actin 1 promoter, nopaline synthase gene promoter, tobacco mosaic virus 35S promoter, and rice-derived actin gene promoter.

It is preferred to use an expression vector carrying a promoter that is specific to a tissue in which an isoprenoid compound is biosynthesized, such as lactiferous ducts. Plant growth retardation and other harmful effects can be reduced by expressing specifically in a tissue in which an isoprenoid is biosynthesized.

Any method for introducing DNA into host plant cells may be used to introduce the recombinant DNA, and examples include methods using *Agrobacterium* (JP S59-140885 A, JP S60-70080 A, WO94/00977, which are incorporated herein by reference), electroporation methods (JP S60-251887 A, incorporated herein by reference), and methods using particle guns (JP 2606856 B, JP 2517813 B, which are incorporated herein by reference).

The transformed plant (transformed plant cells) can be obtained by the above or other methods. The transformed plant conceptually includes not only transformed plant cells obtained by the above methods but also all their progeny or clones and even progeny plants obtained by passaging these cells. Once transformed plant cells into which the DNAs or the vector(s) have been introduced in the genome are obtained, progeny or clones can be obtained from the transformed plant cells by sexual or asexual reproduction, tissue culture, cell culture, cell fusion, or other techniques. Further, the transformed plant cells, or progeny or clones thereof may be used to obtain reproductive materials (e.g. seeds, fruits, cuttings, stem tubers, root tubers, shoots, adventitious buds, adventitious embryos, calluses, protoplasts), which can then be used to produce the transformed plant on a large scale.

Techniques to regenerate plants (transformed plants) from the transformed plant cells are already known; for example, Doi et al. disclose techniques for eucalyptus (JP H11-127025), Fujimura et al. disclose techniques for rice (Fujimura et al., (1995), Plant Tissue Culture Lett., vol. 2: p 74-), Shillito et al. disclose techniques for corn (Shillito et al., (1989), Bio/Technology, vol. 7: p 581-), Visser et al. disclose techniques for potato (Visser et al., (1989), Theor. Appl. Genet., vol. 78: p 589-), and Akama et al. disclose techniques for *Arabidopsis thaliana* (Akama et al., (1992), Plant Cell Rep., vol. 12: p 7-) (all the above documents are incorporated herein by reference). Those skilled in the art can regenerate plants from the transformed plant cells according to these documents.

The expression of the target protein genes in the regenerated plant can be confirmed by known techniques. For example, the expression of the target proteins may be analyzed by Western blot analysis.

Seeds may be obtained from the transformed plant as follows: For example, the transformed plant is rooted in a suitable medium, and the rooted plant is then transplanted into a pot filled with soil containing water. This plant is grown under suitable cultivation conditions until it finally forms seeds, to obtain the seeds. Moreover, plants may be obtained from the seeds as follows: For example, the seeds from the transformed plant obtained as described above may be sown in soil containing water and grown under suitable cultivation conditions to obtain plants.

In the second invention, it is expected that polyisoprenoid productivity can be improved by performing polyisoprenoid production using the transformed plant having introduced therein a gene coding for a CPT family protein, a gene coding for a NgBR family protein, and a gene coding for a REF family protein. Specifically, polyisoprenoid production may be carried out by culturing the transformed plant cells obtained as described above, calluses obtained from the transformed plant cells, cells re-differentiated from the calluses, or the like in a suitable medium, or by growing transformed plants re-differentiated from the transformed plant cells, plants obtained from seeds obtained from the transformed plants, or the like under suitable cultivation conditions.

The polyisoprenoid produced in the method for producing a polyisoprenoid of the second invention can be obtained by harvesting latex from the transformed plant, and subjecting the harvested latex to the following solidification step.

The method for harvesting latex from the transformed plant is not particularly limited, and ordinary harvesting methods may be used. For example, latex may be harvested by collecting the emulsion oozing out from the cuts in the trunk of the plant (tapping), or the emulsion oozing out from the cut roots or other parts of the transformed plant, or by crushing the cut tissue followed by extraction with an organic solvent.

In the solidification step, the method for solidification is not particularly limited, and examples include a method of adding the latex to a solvent that does not dissolve the polyisoprenoid (natural rubber), such as ethanol, methanol or acetone; and a method of adding an acid to the latex. Rubber (natural rubber) can be recovered as solids from the latex by the solidification step. The obtained rubber (natural rubber) may be dried as necessary before use.

Thus, another aspect of the second invention relates to a transformed plant produced by the method for producing a polyisoprenoid of the second invention. The CPT family protein activity in the transformed plant of the second invention is expected to be stabilized and enhanced by the introduced proteins. Therefore, it is expected that the transformed plant exhibits continuously enhanced rubber synthesis activity, and the use of such a transformed plant in polyisoprenoid production can result in an increase in polyisoprenoid production.

The gene coding for a cis-prenyltransferase (CPT) family protein, the gene coding for a Nogo-B receptor (NgBR) family protein, and the gene coding for a rubber elongation factor (REF) family protein in the transformed plant of the second invention, and the plant into which these genes are to be introduced are all as described above.

(Method for Producing Rubber Product)

The method for producing a rubber product of the second invention includes the steps of: kneading a polyisoprenoid produced by the method for producing a polyisoprenoid of the second invention with an additive to obtain a kneaded mixture; forming a raw rubber product from the kneaded mixture; and vulcanizing the raw rubber product.

The rubber product is as described above in connection with the first invention.

When the rubber product is a pneumatic tire, or in other words when the method for producing a rubber product of the second invention is a method for producing a pneumatic tire, the raw rubber product forming step corresponds to a green tire building step in which a green tire is built from the kneaded mixture, and the vulcanization step corresponds to a vulcanization step in which the green tire is vulcanized. Thus, the method for producing a pneumatic tire of the second invention includes the steps of: kneading a polyisoprenoid produced by the method for producing a polyisoprenoid of the second invention with an additive to obtain a kneaded mixture; building a green (or raw) tire from the kneaded mixture; and vulcanizing the green tire.

<Kneading Step>

The kneading step is as described above in connection with the first invention.

<Raw Rubber Product Forming Step (Green Tire Building Step for Tire)>

The raw rubber product forming step is as described above in connection with the first invention.

<Vulcanization Step>

The vulcanization step is as described above in connection with the first invention.

EXAMPLES

The present invention is specifically explained with reference to examples, but the present invention is not limited to these examples.

Example 1

[Extraction of Total RNA from *Hevea* Latex]

Total RNA was extracted from the latex of *Hevea brasiliensis* by the hot phenol method. To 6 mL of the latex were added 6 mL of 100 mM sodium acetate buffer and 1 mL of a 10% SDS solution, and then 12 mL of water-saturated phenol pre-heated at 65° C. The mixture was incubated for 5 minutes at 65° C., agitated in a vortex, and centrifuged at 7000 rpm for 10 minutes at room temperature. After the centrifugation, the supernatant was transferred to a new tube, 12 mL of a phenol:chloroform (1:1) solution was added, and the mixture was agitated by shaking for 2 minutes. After the agitation, the resulting mixture was centrifuged again at 7000 rpm for 10 minutes at room temperature, the supernatant was transferred to a new tube, 12 mL of a chloroform:isoamyl alcohol (24:1) solution was added, and the mixture was agitated by shaking for 2 minutes. After the agitation, the resulting mixture was centrifuged again at 7000 rpm for 10 minutes at room temperature, the supernatant was transferred to a new tube, 1.2 mL of a 3M sodium acetate solution and 13 mL of isopropanol were added, and the mixture was agitated in a vortex. The resulting mixture was incubated for 30 minutes at −20° C. to precipitate total RNA. The incubated mixture was centrifuged at 15000 rpm for 10 minutes at 4° C., and the supernatant was removed to collect a precipitate of total RNA. The collected total RNA was washed twice with 70% ethanol, and dissolved in RNase-free water.

[Synthesis of cDNA from Total RNA]

cDNA was synthesized from the collected total RNA. The cDNA synthesis was carried out using a PrimeScript II 1st strand cDNA synthesis kit (Takara) in accordance with the manual.

[Acquisition of CPT, NgBR and REF Genes from cDNA]

CPT, NgBR and REF genes were obtained using the prepared 1st strand cDNA as a template. PCR was performed using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers:

```
Primer 1:
                                    (SEQ ID NO: 7)
5'-tttggatccgatggaattatacaacggtgagagg-3', Primer 2:
                                    (SEQ ID NO: 8)
5'-tttgcggccgcttattttaagtattccttatgtttctcc-3'.

The NgBR gene was obtained using the following
primers:
Primer 3:
                                    (SEQ ID NO: 9)
5'-tttctcgagatggatttgaaacctggagctg-3', Primer 4:
                                    (SEQ ID NO: 10)
5'-tttctcgagtcatgtaccataattttgctgcac-3'.

The REF gene was obtained using the following
primers:
Primer 5:
                                    (SEQ ID NO: 11)
5'-tttctcgagatggctgaagacgaagac-3', Primer 6:
                                    (SEQ ID NO: 12)
5'-tttggatcctcaattctctccataaaac-3'.
```

CPT gene (HRT1), NgBR gene (HRTBP), and REF gene were obtained as above. The genes were sequenced to identify the full-length nucleotide sequence and amino acid sequence. The nucleotide sequence of HRT1 is given by SEQ ID NO:1. The amino acid sequence of HRT1 is given by SEQ ID NO:2. The nucleotide sequence of HRTBP is given by SEQ ID NO:3. The amino acid sequence of HRTBP is given by SEQ ID NO:4. The nucleotide sequence of REF is given by SEQ ID NO:5. The amino acid sequence of REF is given by SEQ ID NO:6.

[Vector Construction]

The obtained DNA fragments were subjected to dA addition and then inserted into pGEM-T Easy vectors using a pGEM-T Easy Vector System (Promega) to prepare pGEM-HRT1, pGEM-HRTBP, and pGEM-REF.

[Transformation of E. coli]

E. coli DH5α was transformed with the prepared vectors, the transformant was cultured on LB agar medium containing ampicillin and X-gal, and E. coli cells carrying the introduced target genes were selected by blue/white screening.

[Plasmid Extraction]

The E. coli cells transformed with the plasmids containing the target genes were cultured overnight at 37° C. on LB liquid medium. After the culture, the cells were collected, and the plasmids were collected. A FastGene Plasmid mini kit (Nippon Genetics Co., Ltd.) was used for plasmid collection.

It was confirmed by sequence analysis that there were no mutations in the nucleotide sequences of the genes inserted into the collected plasmids.

[Preparation of Vectors for Cell-Free Protein Synthesis]

The pGEM-HRT1 obtained in the above "Vector construction" was treated with the restriction enzymes Bam HI and Not I, and inserted into a pEU-E01-His-TEV-MCS-N2 cell-free expression vector that had been treated similarly with Bam HI and Not I, to prepare pEU-His-N2-HRT1.

Similarly, pGEM-HRTBP was treated with the restriction enzyme Xho I, and inserted into a pEU-E01-MCS-TEV-His-$C_1$ cell-free expression vector that had been treated similarly with Xho I, to prepare pEU-C1-HRTBP.

Furthermore, pGEM-REF was treated with the restriction enzymes Xho I and Bam HI, and inserted into a pEU-E01-MCS-TEV-His-C1 cell-free expression vector that had been treated similarly with Xho I and Bam HI, to prepare pEU-C1-REF.

[Transformation of E. coli]

E. coli DH5α was transformed with the prepared vectors, the transformant was cultured on LB agar medium containing ampicillin and X-gal, and E. coli cells carrying the introduced target genes were selected by colony PCR.

[Plasmid Extraction]

The E. coli cells transformed with the plasmids containing the target genes were cultured overnight at 37° C. on LB liquid medium. After the culture, the cells were collected, and the plasmids were collected. A FastGene Plasmid mini kit (Nippon Genetics Co., Ltd.) was used for plasmid collection.

[Preparation of Rubber Particles]

Rubber particles were prepared from Hevea latex by five stages of centrifugation. To 900 mL of Hevea latex was added 100 mL of 1 M Tris buffer (pH 7.5) containing 20 mM dithiothreitol (DTT) to prepare a latex solution. The latex solution was centrifuged in stages at the following different speeds: 1000×g, 2000×g, 8000×g, 20000×g, and 50000×g. Each stage of centrifugation was carried out for 45 minutes at 4° C. To the rubber particle layer remaining after the centrifugation at 50000×g was added 3-[(3-cholamidopropyl)dimethylamino]-propanesulfonate (CHAPS) at a final concentration of 0.1 to 2.0×CMC (0.1 to 2.0 times the critical micelle concentration CMC) to wash the rubber particles. After the washing, the rubber particles were collected by ultracentrifugation (40000×g, 4° C., 45 minutes), and re-suspended in an equal amount of 100 M Tris buffer (pH 7.5) containing 2 mM dithiothreitol (DTT).

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vectors obtained in the above "Preparation of vectors for cell-free protein synthesis" as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The following amounts were added to a dialysis cup (MWCO 12000, Bio-Teck). A total amount of 60 μL of a reaction solution was prepared according to the protocol of the WEPRO7240H expression kit. To the reaction solution was added 1 to 2 mg of the rubber particles. Separately, 650 μL of SUB-AMIX was added to a No. 2 PP container (Maruemu container).

The dialysis cup was set in the No. 2 PP container, and a protein synthesis reaction was initiated at 26° C. The addition of mRNAs and the replacement of the outer dialysis solution (SUB-AMIX) were performed twice after the initiation of the reaction.

Figure 3:
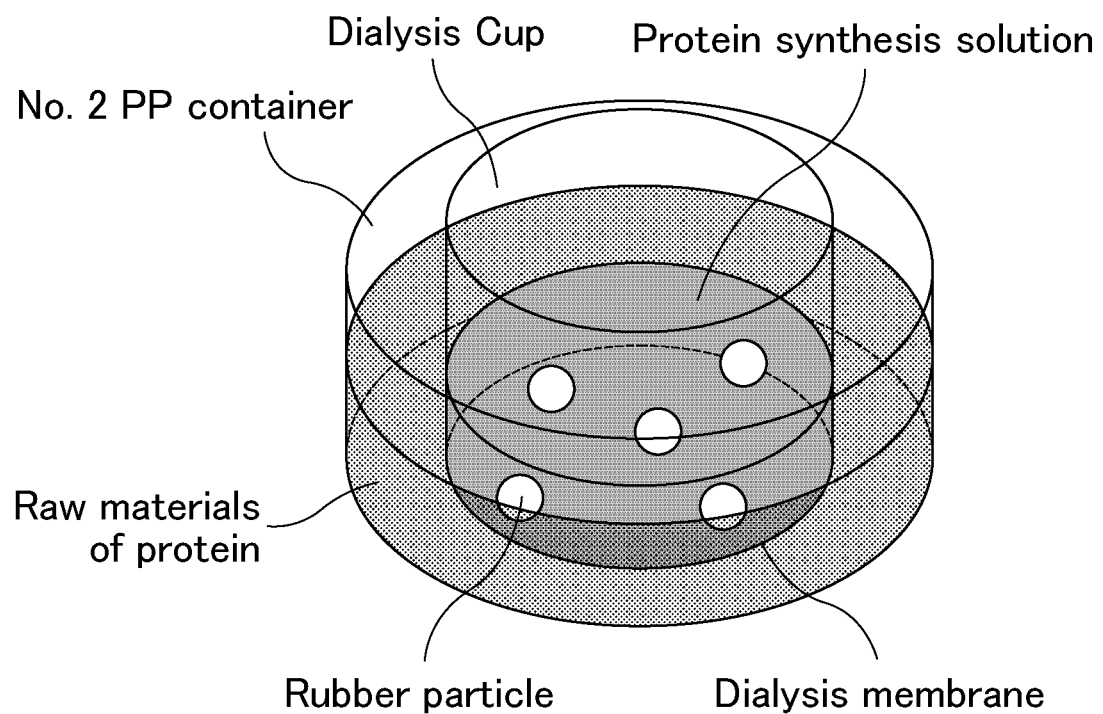
FIG. 3 schematically illustrates the dialysis process in the example.

The reaction was carried out for 24 hours. A schematic diagram illustrating the dialysis process is shown in FIG. 3.

[Collection of Rubber Particles after Reaction]

The solution in the dialysis cup was transferred to a new 1.5 μL tube, and the reacted rubber particles were collected by ultracentrifugation (40000×g, 4° C., 45 minutes) and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the rubber particles collected after the reaction was measured as follows.

First, 50 mM Tris-HCl (pH 7.5), 2 mM DTT, 5 mM $MgCl_2$, 15 μM farnesyl diphosphate (FPP), 100 μM 1-14C isopentenyl diphosphate ([1-14C]IPP, specific activity 5 Ci/mol), and 10 μL of the rubber particle solution were mixed to prepare a reaction solution (100 μL in total), which was then reacted for 16 hours at 30° C.

After the reaction, 200 μL of saturated NaCl was added to the solution, and the mixture was extracted with 1 mL of diethyl ether to extract isopentenol and the like. Next, polyprenyl diphosphates were extracted from the aqueous phase with 1 mL of BuOH saturated with saline, and then an ultra-long-chain polyisoprenoid (natural rubber) was further extracted from the aqueous phase with 1 mL of toluene/hexane (1:1), followed by determination of radioactivity. The radioactivity was determined by $^{14}C$ counting using a liquid scintillation counter. A higher radioactivity (dpm) indicates higher natural rubber production and higher rubber synthesis activity.

The results are shown in Table 1.

Comparative Example 1

[Preparation of Rubber Particles]

Rubber particles were prepared as in Example 1.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the cell-free expression vector pEU-E01-His-TEV-MCS-N2 as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Rubber Particles after Reaction]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the rubber particles collected after the reaction was measured as in Example 1.

Comparative Example 2

The same procedure as in Example 1 was followed but using the pEU-C1-REF obtained in the above "Preparation of vectors for cell-free protein synthesis" in Example 1 as the template for cell-free protein synthesis, and the rubber synthesis activity of the rubber particles collected after the reaction was measured as in Example 1.

The results are shown in Table 1.

Comparative Example 3

The same procedure as in Example 1 was followed but using the pEU-C1-HRTBP obtained in the above "Preparation of vectors for cell-free protein synthesis" in Example 1 as the template for cell-free protein synthesis, and the rubber synthesis activity of the rubber particles collected after the reaction was measured as in Example 1.

The results are shown in Table 1.

Comparative Example 4

The same procedure as in Example 1 was followed but using the pEU-His-N2-HRT1 obtained in the above "Preparation of vectors for cell-free protein synthesis" in Example 1 as the template for cell-free protein synthesis, and the rubber synthesis activity of the rubber particles collected after the reaction was measured as in Example 1.

The results are shown in Table 1.

TABLE 1

|   | Bound protein | Radioactivity (dpm) |
| --- | --- | --- |
| Comparative Example 1 | None | 7500 |
| Comparative Example 2 | REF | 6000 |
| Comparative Example 3 | HRTBP | 5800 |
| Comparative Example 4 | HRT1 | 15000 |
| Example 1 | HRT1 + HRTBP + REF | 25000 |

Table 1 shows that by binding a CPT family protein, a NgBR family protein, and a REF family protein to rubber particles, the rubber synthesis activity of rubber particles was significantly enhanced as compared to when these proteins were bound alone to rubber particles. Further, in Comparative Example 2 in which REF was bound alone to rubber particles and Comparative Example 3 in which NgBR was bound alone to rubber particles, the rubber synthesis activity was lower than in Comparative Example 1 with no bound proteins. From these results it seems that the combination of a CPT family protein, a NgBR family protein, and a REF family protein has a synergistic effect that is greater than the sum of their individual effects. Thus, the rubber synthesis activity of rubber particles is significantly enhanced by the specific combination of a CPT family protein, a NgBR family protein, and a REF family protein, and this effect could not be predicted even by those skilled in the art.

SEQUENCE LISTING FREE TEXT

SEQ ID NO:1: Nucleotide sequence of gene coding for HRT1 from *Hevea brasiliensis*

SEQ ID NO:2: Amino acid sequence of HRT1 from *Hevea brasiliensis*

SEQ ID NO:3: Nucleotide sequence of gene coding for HRTBP from *Hevea brasiliensis*

SEQ ID NO:4: Amino acid sequence of HRTBP from *Hevea brasiliensis*

SEQ ID NO:5: Nucleotide sequence of gene coding for REF from *Hevea brasiliensis*

SEQ ID NO:6: Amino acid sequence of REF from *Hevea brasiliensis*
SEQ ID NO:7: Primer 1
SEQ ID NO:8: Primer 2
SEQ ID NO:9: Primer 3
SEQ ID NO:10: Primer 4
SEQ ID NO:11: Primer 5
SEQ ID NO:12: Primer 6

The invention claimed is:

1. A transformed rubber-producing plant, produced by introducing a gene coding for a cis-prenyltransferase (CPT) family protein, a gene coding for a Nogo-B receptor (NgBR) family protein, and a gene coding for a rubber elongation factor (REF) family protein into a plant selected from the group consisting of Hevea brasiliensis, Taraxacum koksaghyz, Parthenium argentatum, Sonchus oleraceus, Helianthus annuus, Lactuca sativa, and Ficus elastica by using a vector that contains a heterologous promoter to allow the plant to express the CPT family protein, the NgBR family protein, and the REF family protein.

2. The transformed rubber-producing plant according to claim 1,
wherein at least one gene selected from the group consisting of the gene coding for a cis-prenyltransferase (CPT) family protein, the gene coding for a Nogo-B receptor (NgBR) family protein, and the gene coding for a rubber elongation factor (REF) family protein is derived from a plant.

3. The transformed rubber-producing plant according to claim 2,
wherein at least one gene selected from the group consisting of the gene coding for a cis-prenyltransferase (CPT) family protein, the gene coding for a Nogo-B receptor (NgBR) family protein, and the gene coding for a rubber elongation factor (REF) family protein is derived from Hevea brasiliensis.

4. The transformed rubber-producing plant according to claim 1,
wherein the gene coding for a cis-prenyltransferase (CPT) family protein is the following DNA [1] or [2]:

[1] a DNA comprising the nucleotide sequence of SEQ ID NO:1; or

[2] a DNA that hybridizes under stringent conditions with a DNA comprising a nucleotide sequence complementary to the nucleotide sequence of SEQ ID NO:1, and codes for a protein having an enzyme activity that catalyzes a reaction of cis-chain elongation of an isoprenoid compound.

5. The transformed rubber-producing plant according to claim 1,
wherein the gene coding for a Nogo-B receptor (NgBR) family protein is the following DNA [3] or [4]:

[3] a DNA comprising the nucleotide sequence of SEQ ID NO:3; or

[4] a DNA that hybridizes under stringent conditions with a DNA comprising a nucleotide sequence complementary to the nucleotide sequence of SEQ ID NO:3, and codes for a protein having the functions of binding to a membrane via one or more transmembrane domains on the N-terminal side of the protein, and interacting with another protein on the C-terminal side thereof.

6. The transformed rubber-producing plant according to claim 1,
wherein the gene coding for a rubber elongation factor (REF) family protein is the following DNA [5] or [6]:

[5] a DNA comprising the nucleotide sequence of SEQ ID NO:5; or

[6] a DNA that hybridizes under stringent conditions with a DNA comprising a nucleotide sequence complementary to the nucleotide sequence of SEQ ID NO:5, and codes for a rubber particle-associated protein that is bound to rubber particles in latex.

* * * * *

```
                        SEQUENCE LISTING

<160> NUMBER OF SEQ ID NOS: 12

<210> SEQ ID NO 1
<211> LENGTH: 873
<212> TYPE: DNA
<213> ORGANISM: Hevea brasiliensis

<400> SEQUENCE: 1
atggaattat acaacggtga gaggccaagt gtgttcagac ttttagggaa gtatatgaga     60
aaagggttat atagcatcct aacccagggt cccatcccta ctcatattgc cttcatattg    120
gatggaaaca ggaggtttgc taagaagcat aaactgccag aaggaggtgg tcataaggct    180
ggatttttag ctcttctgaa cgtactaact tattgctatg agttaggagt gaaatatgcg    240
actatctatg cctttagcat cgataatttt cgaaggaaac tcatgaggt tcagtacgta     300 atggatctaa tgctggagaa gattgaaggg atgatcatgg aagaaagtat catcaatgca    360
tatgatattt gcgtacgttt tgtgggtaac ctgaagcttt taagtgagcc agtcaagacc    420
gcagcagata agattatgag ggctactgcc aacaattcca aatgtgtgct tctcattgct    480
gtatgctata cttcaactga tgagatcgtg catgctgttg aagaatcctc tgaattgaac    540
tccaatgaag tttgtaacaa tcaagaattg gaggaggcaa atgcaactgg aagcggtact    600
gtgattcaaa ttgagaacat ggagtcgtat tctggaataa aacttgtaga ccttgagaaa    660
aacacctaca taaatcctta tcctgatgtt ctgattcgaa cttctgggga gacccgtctg    720
agcaactact tactttggca gactactaat tgcatactgt attctcctca tgcactgtgg    780
ccagagattg gtcttcgaca cgtggtgtgg gcagtaatta acttccaacg tcattattct    840
tacttggaga aacataagga atacttaaaa taa                                 873

<210> SEQ ID NO 2
<211> LENGTH: 290
<212> TYPE: PRT
<213> ORGANISM: Hevea brasiliensis

<400> SEQUENCE: 2

Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Arg Arg Phe Ala Lys
        35                  40                  45

Lys His Lys Leu Pro Glu Gly Gly Gly His Lys Ala Gly Phe Leu Ala
    50                  55                  60

Leu Leu Asn Val Leu Thr Tyr Cys Tyr Glu Leu Gly Val Lys Tyr Ala
65                  70                  75                  80

Thr Ile Tyr Ala Phe Ser Ile Asp Asn Phe Arg Arg Lys Pro His Glu
                85                  90                  95

Val Gln Tyr Val Met Asp Leu Met Leu Glu Lys Ile Glu Gly Met Ile
            100                 105                 110

Met Glu Glu Ser Ile Ile Asn Ala Tyr Asp Ile Cys Val Arg Phe Val
        115                 120                 125

Gly Asn Leu Lys Leu Leu Ser Glu Pro Val Lys Thr Ala Ala Asp Lys
```

```
                130             135             140
Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Gly Thr Val Ile Gln Ile Glu Asn Met Glu
            195                 200                 205

Ser Tyr Ser Gly Ile Lys Leu Val Asp Leu Glu Lys Asn Thr Tyr Ile
        210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

His Ala Leu Trp Pro Glu Ile Gly Leu Arg His Val Val Trp Ala Val
            260                 265                 270

Ile Asn Cys Gln Arg His Tyr Ser Tyr Leu Glu Lys His Lys Glu Tyr
        275                 280                 285

Leu Lys
    290

<210> SEQ ID NO 3
<211> LENGTH: 774
<212> TYPE: DNA
<213> ORGANISM: Hevea brasiliensis

<400> SEQUENCE: 3
atggatttga aacctggagc tggagggcag agagttaatc gattagtgga tccgattagt      60
tatcattttc ttcaatttct gtggcgtact ctacatcttc ttgtcagctt atggtacctt     120
caagttagta tggtccaaat gatcgaaggc tttctaatct ctagtggact tgtgaaacgc     180
tatggagccc tcgatattga caaggtccgg taccttgcca ttgtggtaga tagtgaagaa     240
gcttaccaaa tttctaaagt tattcagctt ttgaaatggg tggaagatat gggtgtgaaa     300
catttatgcc tctatgattc aaaaggagtt ctcaagacaa acaagaaaac catcatggag     360
agtttgaaca atgctatgcc atttgaggaa gcagttgaaa aagatgtttt actggaccag     420
aaacagatga ctgtggaatt tgcttccagc tccgatggaa aggaagcaat aaccagggca     480
gctaacgtac tctttatgaa gtatttgaag atgctaaaaa ctggtgtagg aaaggaagaa     540
ccatgcttta cagaagatca aatggatgag gcactaaaag ctataggtta caaagggccg     600
gaacctgact tgctattaat ttatggacct gttagatgcc atctaggttt ctcaccgtgg     660
agacttcgat atactgagat ggtgcatatg ggacccttga ggtacatgaa cctcggttca     720
ctaaaaaagg ccattcacag gttcacaaca gtgcagcaaa attatggtac atga          774

<210> SEQ ID NO 4
<211> LENGTH: 257
<212> TYPE: PRT
<213> ORGANISM: Hevea brasiliensis

<400> SEQUENCE: 4

Met Asp Leu Lys Pro Gly Ala Gly Gly Gln Arg Val Asn Arg Leu Val
1               5                   10                  15

Asp Pro Ile Ser Tyr His Phe Leu Gln Phe Leu Trp Arg Thr Leu His
            20                  25                  30
```

```
Leu Leu Val Ser Leu Trp Tyr Leu Gln Val Ser Met Val Gln Met Ile
            35                  40                  45

Glu Gly Phe Leu Ile Ser Ser Gly Leu Val Lys Arg Tyr Gly Ala Leu
 50                  55                  60

Asp Ile Asp Lys Val Arg Tyr Leu Ala Ile Val Asp Ser Glu Glu
65                  70                  75                  80

Ala Tyr Gln Ile Ser Lys Val Ile Gln Leu Leu Lys Trp Val Glu Asp
                85                  90                  95

Met Gly Val Lys His Leu Cys Leu Tyr Asp Ser Lys Gly Val Leu Lys
            100                 105                 110

Thr Asn Lys Lys Thr Ile Met Glu Ser Leu Asn Asn Ala Met Pro Phe
                115                 120                 125

Glu Glu Ala Val Glu Lys Asp Val Leu Leu Asp Gln Lys Gln Met Thr
130                 135                 140

Val Glu Phe Ala Ser Ser Ser Asp Gly Lys Glu Ala Ile Thr Arg Ala
145                 150                 155                 160

Ala Asn Val Leu Phe Met Lys Tyr Leu Lys Tyr Ala Lys Thr Gly Val
                165                 170                 175

Gly Lys Glu Glu Pro Cys Phe Thr Glu Asp Gln Met Asp Glu Ala Leu
            180                 185                 190

Lys Ala Ile Gly Tyr Lys Gly Pro Glu Pro Asp Leu Leu Leu Ile Tyr
            195                 200                 205

Gly Pro Val Arg Cys His Leu Gly Phe Ser Pro Trp Arg Leu Arg Tyr
210                 215                 220

Thr Glu Met Val His Met Gly Pro Leu Arg Tyr Met Asn Leu Gly Ser
225                 230                 235                 240

Leu Lys Lys Ala Ile His Arg Phe Thr Thr Val Gln Gln Asn Tyr Gly
                245                 250                 255

Thr

<210> SEQ ID NO 5
<211> LENGTH: 417
<212> TYPE: DNA
<213> ORGANISM: Hevea brasiliensis

<400> SEQUENCE: 5
atggctgaag acgaagacaa ccaacaaggg caggggagg ggttaaaata tttgggtttt      60
gtgcaagacg cggcaactta tgctgtgact accttctcaa acgtctatct ttttgccaaa     120
gacaaatctg gtccactgca gcctggtgtc gatatcattg agggtccggt gaagaacgtg     180
gctgtacctc tctataatag gttcagttat attcccaatg gagctctcaa gtttgtagac     240
agcacggttg ttgcatctgt cactattata gatcgctctc ttccccccaat tgtcaaggac     300 gcatctatcc aagttgtttc agcaattcga gctgccccag aagctgctcg ttctctggct     360
tcttctttgc ctgggcagac caagatactt gctaaggtgt tttatggaga gaattga       417

<210> SEQ ID NO 6
<211> LENGTH: 138
<212> TYPE: PRT
<213> ORGANISM: Hevea brasiliensis

<400> SEQUENCE: 6

Met Ala Glu Asp Glu Asp Asn Gln Gln Gly Gln Gly Glu Gly Leu Lys
1               5                   10                  15

Tyr Leu Gly Phe Val Gln Asp Ala Ala Thr Tyr Ala Val Thr Thr Phe
```

-continued

```
                    20                  25                  30
Ser Asn Val Tyr Leu Phe Ala Lys Asp Lys Ser Gly Pro Leu Gln Pro
             35                  40                  45

Gly Val Asp Ile Ile Glu Gly Pro Val Lys Asn Val Ala Val Pro Leu
     50                  55                  60

Tyr Asn Arg Phe Ser Tyr Ile Pro Asn Gly Ala Leu Lys Phe Val Asp
 65                  70                  75                  80

Ser Thr Val Val Ala Ser Val Thr Ile Ile Asp Arg Ser Leu Pro Pro
                 85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
         115                 120                 125

Ile Leu Ala Lys Val Phe Tyr Gly Glu Asn
        130                 135

<210> SEQ ID NO 7
<211> LENGTH: 34
<212> TYPE: DNA
<213> ORGANISM: Artificial Sequence
<220> FEATURE:
<223> OTHER INFORMATION: PRIMER-1

<400> SEQUENCE: 7
tttggatccg atggaattat acaacggtga gagg                              34

<210> SEQ ID NO 8
<211> LENGTH: 39
<212> TYPE: DNA
<213> ORGANISM: Artificial Sequence
<220> FEATURE:
<223> OTHER INFORMATION: PRIMER-2

<400> SEQUENCE: 8
tttgcggccg cttattttaa gtattcctta tgtttctcc                         39

<210> SEQ ID NO 9
<211> LENGTH: 31
<212> TYPE: DNA
<213> ORGANISM: Artificial Sequence
<220> FEATURE:
<223> OTHER INFORMATION: PRIMER-3

<400> SEQUENCE: 9
tttctcgaga tggatttgaa acctggagct g                                 31

<210> SEQ ID NO 10
<211> LENGTH: 33
<212> TYPE: DNA
<213> ORGANISM: Artificial Sequence
<220> FEATURE:
<223> OTHER INFORMATION: PRIMER-4

<400> SEQUENCE: 10
tttctcgagt catgtaccat aattttgctg cac                               33

<210> SEQ ID NO 11
<211> LENGTH: 27
<212> TYPE: DNA
<213> ORGANISM: Artificial Sequence
<220> FEATURE:
<223> OTHER INFORMATION: PRIMER-5
```

```
<400> SEQUENCE: 11
tttctcgaga tggctgaaga cgaagac                                            27

<210> SEQ ID NO 12
<211> LENGTH: 28
<212> TYPE: DNA
<213> ORGANISM: Artificial Sequence
<220> FEATURE:
<223> OTHER INFORMATION: PRIMER-6

<400> SEQUENCE: 12
tttggatcct caattctctc cataaaac                                           28
```